United States Patent
Schwizer et al.

(10) Patent No.: US 11,724,988 B2
(45) Date of Patent: Aug. 15, 2023

(54) PROCESSES

(71) Applicant: INFLAZOME LIMITED, Dublin (IE)

(72) Inventors: Daniel Schwizer, Bubendorf (CH);
Sascha Breeger, Bubendorf (CH);
Stephen Thom, Nottingham (GB);
Thomas Alanine, Nottingham (GB)

(73) Assignee: INFLAZOME LIMITED, Dublin (IE)

( * ) Notice: Subject to any disclaimer, the term of this patent is extended or adjusted under 35 U.S.C. 154(b) by 0 days.

(21) Appl. No.: 17/286,380

(22) PCT Filed: Oct. 18, 2019

(86) PCT No.: PCT/EP2019/078325
§ 371 (c)(1),
(2) Date: Apr. 16, 2021

(87) PCT Pub. No.: WO2020/079207
PCT Pub. Date: Apr. 23, 2020

(65) Prior Publication Data
US 2022/0064125 A1 Mar. 3, 2022

(30) Foreign Application Priority Data
Oct. 19, 2018 (GB) .................................. 1817038.1

(51) Int. Cl.
*C07D 231/08* (2006.01)
*C07C 209/36* (2006.01)

(52) U.S. Cl.
CPC .......... *C07D 231/08* (2013.01); *C07C 209/36* (2013.01); *C07C 2603/10* (2017.05)

(58) Field of Classification Search
CPC .. C07D 231/08; C07C 209/36; C07C 2603/10
See application file for complete search history.

(56) References Cited

U.S. PATENT DOCUMENTS

| | | |
|---|---|---|
| 10,538,487 B2 | 1/2020 | O'Neill et al. |
| 10,973,803 B2 | 4/2021 | Miller et al. |
| 2012/0220461 A1 | 8/2012 | Kusuoka et al. |
| 2019/0359564 A1 | 11/2019 | O'Neill et al. |

FOREIGN PATENT DOCUMENTS

| | | |
|---|---|---|
| EP | 3606909 B1 | 5/2020 |
| WO | WO 2014/002111 A1 | 1/2014 |
| WO | WO 2016/131098 A1 | 8/2016 |
| WO | WO 2018/015445 A1 | 1/2018 |
| WO | WO 2019/206871 A1 | 10/2019 |
| WO | WO 2020/079207 A1 | 4/2020 |

OTHER PUBLICATIONS

Salla, et al., "Identification, Synthesis, and Biological Evaluation of the Major Human Metabolite of NLRP3 Inflammasome Inhibitor MCC950," ACS Medicinal Chemistry Letters, vol. 7, No. 12, pp. 1034-1038, (Sep. 27, 2016).
WIPO Application No. PCT/EP2019/078325, PCT International Search Report and Written Opinion of the International Searching Authority dated Feb. 4, 2020.
WIPO Application No. PCT/EP2019/078325, International Preliminary Reporton Patentability dated Apr. 14, 2021.
Himiceskij, Chemical Encyclopedia, (1983), pp. 130-131 [and brief statement of relevance in English].
Solvation—Wikipedia, retrieved from the internet on Jan. 15, 2022 at: https://en.wikipedia.org/wiki/Solvation.

*Primary Examiner* — Sikarl A Witherspoon
(74) *Attorney, Agent, or Firm* — Alston & Bird LLP

(57) ABSTRACT

The present invention relates to processes of preparing N-((1,2,3,4,5,6,7-hexahydro-s-indacen-4-yl)carbamoyl)-1-iso-propyl-1H-pyrazole-3-sulfonamide and salts thereof. The present invention further relates to pharmaceutical compositions comprising such compounds and to the use of such compounds in the treatment and prevention of medical disorders and diseases, most especially by NLRP3 inhibition.

11 Claims, No Drawings

PROCESSES

CROSS-REFERENCE TO RELATED APPLICATIONS

This application is a national stage entry of PCT/EP2019/078325 filed Oct. 18, 2019, which claims the benefit of GB1817038.1 filed Oct. 19, 2018.

FIELD OF THE INVENTION

The present invention relates to processes of preparing N-((1,2,3,5,6,7-hexahydro-s-indacen-4-yl)carbamoyl)-1-isopropyl-1H-pyrazole-3-sulfonamide and salts thereof. The present invention further relates to pharmaceutical compositions comprising such compounds and to the use of such compounds in the treatment and prevention of medical disorders and diseases, most especially by NLRP3 inhibition.

BACKGROUND

N-((1,2,3,5,6,7-Hexahydro-s-indacen-4-yl)carbamoyl)-1-isopropyl-1H-pyrazole-3-sulfonamide has been disclosed in WO 2016/131098 A1 as an NLRP3 inhibitor. However, there is a need to provide improved processes for preparing N-((1,2,3,5,6,7-hexahydro-s-indacen-4-yl)carbamoyl)-1-isopropyl-1H-pyrazole-3-sulfonamide and salts thereof, which provide N-((1,2,3,5,6,7-hexahydro-s-indacen-4-yl)carbamoyl)-1-isopropyl-1H-pyrazole-3-sulfonamide and salts thereof on a larger scale and/or at a higher yield and/or with a higher purity compared to prior art processes.

SUMMARY OF THE INVENTION

A first aspect of the present invention provides a process of preparing N-((1,2,3,5,6,7-hexahydro-s-indacen-4-yl)carbamoyl)-1-isopropyl-1H-pyrazole-3-sulfonamide or a salt thereof, comprising the step of contacting 1-isopropyl-3-(alkoxycarbonylamino-sulfonyl)-1H-pyrazole with 1,2,3,5,6,7-hexahydro-s-indacen-4-amine in the presence of a solvent to obtain N-((1,2,3,5,6,7-hexahydro-s-indacen-4-yl)carbamoyl)-1-isopropyl-1H-pyrazole-3-sulfonamide:

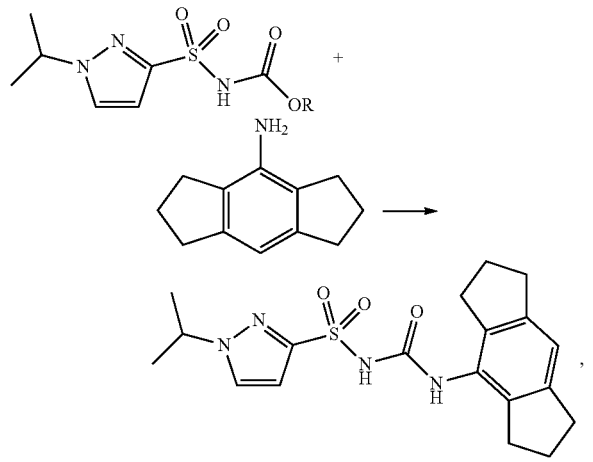

wherein R is $C_{1-6}$ alkyl.

In one embodiment, R is selected from methyl, ethyl and propyl. Typically R is methyl. When R is methyl, there is provided a process of preparing N-((1,2,3,5,6,7-hexahydro-s-indacen-4-yl)carbamoyl)-1-isopropyl-1H-pyrazole-3-sulfonamide or a salt thereof, comprising the step of contacting 1-isopropyl-3-(methoxycarbonylaminosulfonyl)-1H-pyrazole with 1,2,3,5,6,7-hexahydro-s-indacen-4-amine in the presence of a solvent to obtain N-((1,2,3,5,6,7-hexahydro-s-indacen-4-yl)carbamoyl)-1-isopropyl-1H-pyrazole-3-sulfonamide:

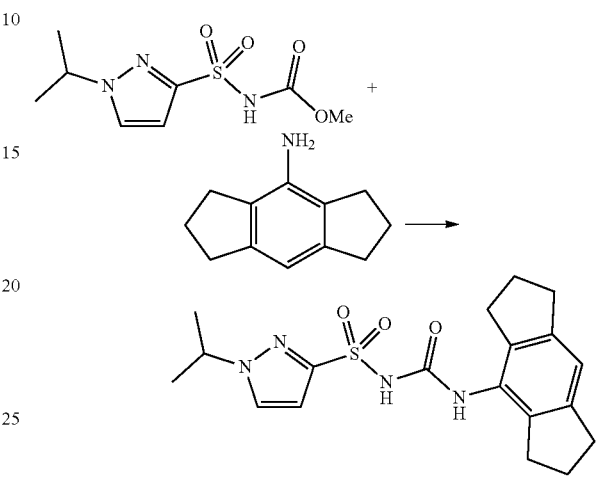

In one embodiment of the first aspect of the present invention, the solvent comprises dimethyl carbonate, methyl ethyl ketone, acetone, tert-butyl acetate, ethyl acetate, toluene, or a mixture thereof. Typically, the solvent comprises dimethyl carbonate.

In one embodiment of the first aspect of the present invention, the reaction is carried out at a temperature of 40-95° C. Typically, the reaction is carried out at a temperature of 50-95° C. Typically, the reaction mixture is heated at a temperature of 70-95° C. for 10-40 hours.

Compared to similar prior art processes, the process of the first aspect of the present invention has a reproducibly high yield, is conducted using mild reaction conditions, provides product with excellent HPLC purity, and is therefore suitable for large scale clinical manufacture.

In one embodiment of the first aspect of the present invention, the 1-isopropyl-3-(alkoxycarbonylaminosulfonyl)-1H-pyrazole is prepared by a process according to the second aspect of the present invention.

In one embodiment of the first aspect of the present invention, the 1,2,3,5,6,7-hexahydro-s-indacen-4-amine is prepared by a process according to the third aspect of the present invention.

A second aspect of the present invention provides a process of preparing 1-isopropyl-3-(alkoxycarbonylaminosulfonyl)-1H-pyrazole:

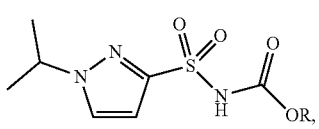

wherein R is $C_{1-6}$ alkyl, comprising one or more steps selected from:

(a) contacting 3-nitro-1H-pyrazole with iPr-X to obtain 1-isopropyl-3-nitro-1H-pyrazole, wherein X is a leaving group:

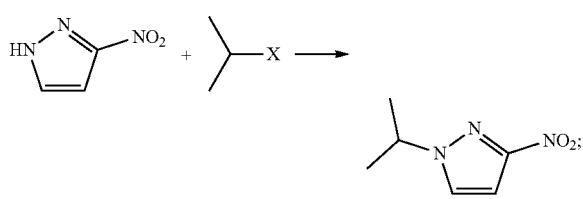

(b) reducing 1-isopropyl-3-nitro-1H-pyrazole to obtain 1-isopropyl-3-amino-1H-pyrazole:

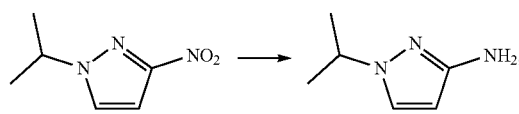

(c) converting 1-isopropyl-3-amino-1H-pyrazole into 1-isopropyl-3-iodo-1H-pyrazole:

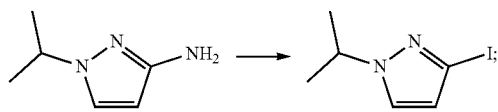

(d) converting 1-isopropyl-3-iodo-1H-pyrazole into 1-isopropyl-1H-pyrazole-3-sulfonamide:

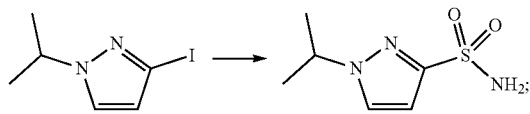

and (e) converting 1-isopropyl-1H-pyrazole-3-sulfonamide into 1-isopropyl-3-(alkoxycarbonylaminosulfonyl)-1H-pyrazole:

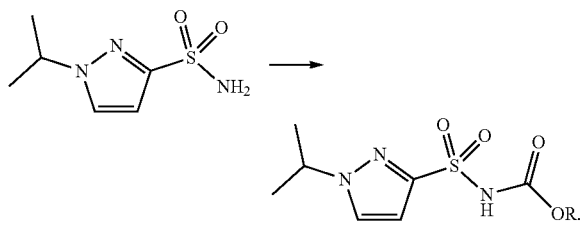

In one embodiment, R is selected from methyl, ethyl and propyl. Typically, R is methyl. When R is methyl, there is provided a process of preparing 1-isopropyl-3-(methoxycarbonylaminosulfonyl)-1H-pyrazole.

In one embodiment, the process comprises one, two, three, four or all five of steps (a) to (e). Typically, the process comprises steps (d) and (e). The process may comprise steps (c), (d) and (e). The process may comprise steps (b), (c), (d) and (e). The process may comprise steps (a), (b), (c), (d) and (e).

When the process comprises steps (d) and (e), the 1-isopropyl-3-iodo-1H-pyrazole required for step (d) may be obtained by steps (a), (b) and (c), or by any other process.

Compared to similar prior art processes, the processes of steps (a), (b), (c), (d) and (e) have a reproducibly high yield, are conducted using mild, non-toxic reagents and mild reaction conditions, provide product with excellent HPLC purity, and are therefore suitable for large scale clinical manufacture.

Therefore the second aspect of the present invention also provides 1-isopropyl-3-(alkoxycarbonylaminosulfonyl)-1H-pyrazole:

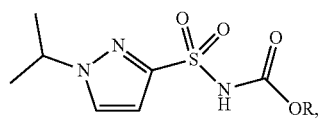

wherein R is $C_{1-6}$ alkyl.

Typically, the 1-isopropyl-3-(alkoxycarbonylaminosulfonyl)-1H-pyrazole has a HPLC purity of 98% or more, or 98.5% or more, or 99% or more, or 99.5% or more, or 99.6% or more, or 99.7% or more.

In one embodiment, R is selected from methyl, ethyl and propyl. Typically, R is methyl. When R is methyl, the second aspect of the present invention provides 1-isopropyl-3-(methoxycarbonylaminosulfonyl)-1H-pyrazole.

In one embodiment, in step (a), the leaving group X is selected from fluorine, chlorine, bromine, iodine, toluenesulfonyl, methanesulfonyl and trifluoromethanesulfonyl. Typically, X is a leaving group selected from chlorine, bromine and iodine. Typically, X is a leaving group selected from bromine and iodine. More typically, X is iodine.

In one embodiment, in step (a), 3-nitro-1H-pyrazole is contacted with iPr-X in the presence of a base. Typically, the base is an inorganic base. Typically, the base comprises potassium carbonate, sodium carbonate, potassium hydroxide, sodium hydroxide, potassium tert-butoxide, sodium tert-butoxide, or a mixture thereof. More typically, the base comprises potassium carbonate.

Step (a) may be carried out in the presence of a solvent. Typically, the solvent is an aprotic solvent. Typically, the solvent is a polar solvent. Typically, the solvent is a polar aprotic solvent. Typically, the solvent comprises acetonitrile, THF, DMF, HMPA, DMSO, N-methylpyrrolidone, methyl ethyl ketone, tert-butyl acetate, ethyl acetate, acetone, propylene carbonate, or a mixture thereof. Typically, the solvent comprises acetonitrile.

In one embodiment, the reaction of step (a) is carried out at a temperature of 10-80° C. Typically, the reaction of step (a) is carried out at a temperature of 30-70° C.

In one embodiment, the reduction of step (b) is carried out using a catalyst and hydrogen gas. Typically, the catalyst is a metal catalyst comprising platinum, palladium, rhodium, ruthenium or nickel. Typically, the catalyst is Pd/C, Pd(OH)$_2$, Pt/C, PtO$_2$, platinum black or Raney nickel. More typically, the catalyst is Pd/C or Pd(OH)$_2$. Typically, the hydrogen gas is used at a pressure of 80-120 Psi, typically about 100 Psi. The catalyst and hydrogen gas may be used in the presence of an acid such as sulfuric acid or methanesulfonic acid.

Alternatively, the reduction of step (b) is carried out using a metal and a source of hydrogen. Typically, the metal is Zn dust or iron. Typically, the source of hydrogen is sulfuric acid, acetic acid, formic acid, ammonium formate or ammonium chloride.

In one embodiment, the reduction of step (b) is carried out in the presence of a solvent. Typically, the solvent is a polar solvent. Typically, the solvent comprises methanol, ethanol, isopropanol, n-butanol, THF, water, ethyl acetate, acetic acid, or a mixture thereof. Typically, the solvent comprises methanol, ethanol, THF, water, or a mixture thereof.

In one embodiment, the reduction of step (b) is carried out at a temperature of 10-80° C. Typically, the reduction of step (b) is carried out at a temperature of 20-60° C.

In one embodiment, in step (c), 1-isopropyl-3-amino-1H-pyrazole is converted into a diazonium intermediate which in turn is converted into 1-isopropyl-3-iodo-1H-pyrazole. Typically, 1-isopropyl-3-amino-1H-pyrazole is converted into a diazonium intermediate using sodium nitrite and an acid such as sulfuric acid, hydrochloric acid or $HBF_4$. More typically, 1-isopropyl-3-amino-1H-pyrazole is converted into a diazonium intermediate using an aqueous solution of sulfuric acid and sodium nitrite. Typically, the diazonium intermediate is converted into 1-isopropyl-3-iodo-1H-pyrazole using potassium iodide or sodium iodide. More typically, the diazonium intermediate is converted into 1-isopropyl-3-iodo-1H-pyrazole using potassium iodide.

Step (c) may be carried out in the presence of a solvent. In one embodiment, the solvent is a polar solvent. In one embodiment, the solvent is a polar aprotic solvent, such as acetonitrile, THF, DMF, HMPA, DMSO, N-methylpyrrolidone, methyl ethyl ketone, tert-butyl acetate, ethyl acetate, acetone, propylene carbonate, or a mixture thereof. Typically, the polar aprotic solvent comprises acetonitrile. In one embodiment, the solvent is a polar protic solvent, such as methanol, ethanol, isopropanol, n-butanol, water, or a mixture thereof. Typically, the polar protic solvent comprises water. In one embodiment, the solvent is a mixture of a polar protic solvent and a polar aprotic solvent, such as a mixture of water and acetonitrile.

In one embodiment, the reaction of step (c) is carried out at a temperature of −20 to 20° C. Typically, the reaction of step (c) is carried out at a temperature of −10 to 10° C.

In one embodiment, in step (d), 1-isopropyl-3-iodo-1H-pyrazole is converted into 1-isopropyl-1H-pyrazole-3-sulfonamide by treatment with a Grignard reagent or an organolithium reagent, followed by treatment with sulfur dioxide gas, followed by treatment with hydroxylamine-O-sulfonic acid.

Typically, the Grignard reagent is isopropyl magnesium chloride or isopropyl magnesium chloride lithium chloride complex. More typically, the Grignard reagent is isopropyl magnesium chloride. Typically, the organolithium reagent is isopropyl lithium. Typically, the hydroxylamine-O-sulfonic acid is provided as aqueous hydroxylamine-O-sulfonic acid in the presence of trisodium citrate.

Step (d) may be carried out in the presence of a solvent. In one embodiment, the solvent is an aprotic solvent. In one embodiment, the solvent is an aprotic polar solvent, such as 2-methyltetrahydrofuran, acetonitrile, THF, DMF, HMPA, DMSO, N-methylpyrrolidone, methyl ethyl ketone, tert-butyl acetate, ethyl acetate, acetone, propylene carbonate, or a mixture thereof. Typically, the aprotic polar solvent comprises 2-methyltetrahydrofuran. In one embodiment, the solvent is an aprotic hydrocarbon solvent, such as n-pentane, n-hexane, n-heptane, toluene, or a mixture thereof. Typically, the aprotic hydrocarbon solvent comprises n-heptane. In one embodiment, the solvent is a mixture of an aprotic polar solvent and an aprotic hydrocarbon solvent, such as a mixture of 2-methyltetrahydrofuran and n-heptane.

In one embodiment, the reaction of step (d) is carried out at a temperature of 5-40° C. Typically, the reaction of step (d) is carried out at a temperature of 5-25° C.

In one embodiment, in step (e), 1-isopropyl-1H-pyrazole-3-sulfonamide is converted into 1-isopropyl-3-(alkoxycarbonylaminosulfonyl)-1H-pyrazole by treatment with a carbonate in the presence of a base.

In one embodiment, in step (e), the carbonate is selected from dimethyl carbonate, diethyl carbonate, dimethyl pyrocarbonate, and diethyl pyrocarbonate. Typically, the carbonate is dimethyl carbonate or dimethyl pyrocarbonate. More typically, the carbonate is dimethyl carbonate.

In one embodiment, in step (e), the base is an inorganic base. Typically, the base comprises sodium methoxide, sodium ethoxide, potassium methoxide, potassium ethoxide, sodium hydroxide, potassium hydroxide, sodium carbonate, potassium carbonate, potassium tert-butoxide, sodium tert-butoxide, or a mixture thereof. More typically, the base comprises sodium methoxide.

Step (e) may be carried out in the presence of a solvent. Typically, the solvent is an alcoholic solvent. Typically, the solvent comprises methanol, ethanol, isopropanol, n-butanol, or a mixture thereof. Typically, the solvent comprises methanol.

In one embodiment, the reaction of step (e) is carried out at a temperature of 10-80° C. Typically, the reaction of step (e) is carried out at a temperature of 30-65° C.

In one specific embodiment of the second aspect of the present invention, there is provided a process of preparing 1-isopropyl-3-(methoxycarbonylaminosulfonyl)-1H-pyrazole:

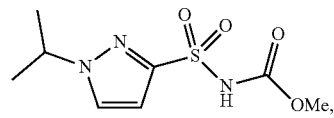 [SMILES: COC(=O)NS(=O)(=O)c1ccn(C(C)C)n1]

comprising the steps of:

(d) converting 1-isopropyl-3-iodo-1H-pyrazole into 1-isopropyl-1H-pyrazole-3-sulfonamide by treatment with a Grignard reagent or an organolithium reagent, followed by treatment with sulfur dioxide gas, followed by treatment with hydroxylamine-O-sulfonic acid:

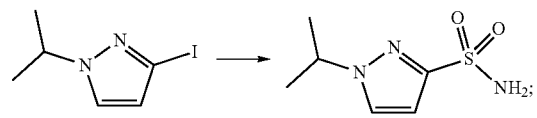

and (e) converting 1-isopropyl-1H-pyrazole-3-sulfonamide into 1-isopropyl-3-(methoxycarbonylaminosulfonyl)-1H-pyrazole by treatment with dimethyl carbonate or dimethyl pyrocarbonate in the presence of a base:

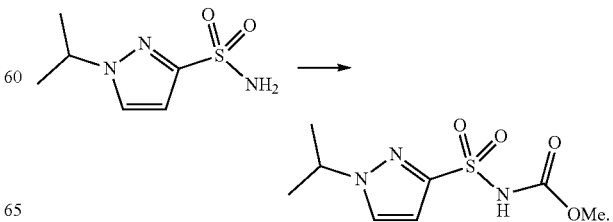

In another specific embodiment of the second aspect of the present invention, there is provided a process of preparing 1-isopropyl-3-(methoxycarbonylaminosulfonyl)-1H-pyrazole:

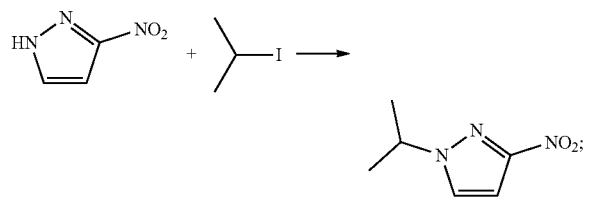

comprising the steps of:

(a) contacting 3-nitro-1H-pyrazole with 2-iodo-propane in the presence of a base to obtain 1-isopropyl-3-nitro-1H-pyrazole:

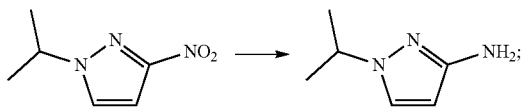

(b) reducing 1-isopropyl-3-nitro-1H-pyrazole to obtain 1-isopropyl-3-amino-1H-pyrazole:

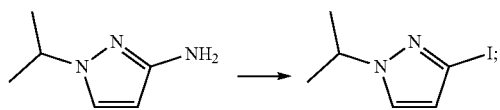

(c) converting 1-isopropyl-3-amino-1H-pyrazole into 1-isopropyl-3-iodo-1H-pyrazole by treatment with an aqueous solution of sulfuric acid and sodium nitrite, followed by treatment with potassium iodide:

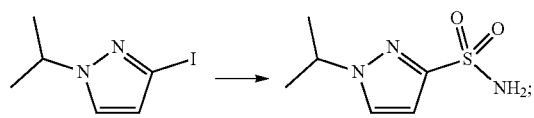

(d) converting 1-isopropyl-3-iodo-1H-pyrazole into 1-isopropyl-1H-pyrazole-3-sulfonamide by treatment with a Grignard reagent or an organolithium reagent, followed by treatment with sulfur dioxide gas, followed by treatment with hydroxylamine-O-sulfonic acid:

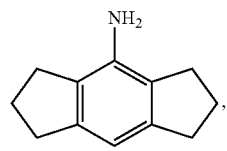 [SMILES: Nc1c2c(cc3c1CCC3)CCC2]

and (e) converting 1-isopropyl-1H-pyrazole-3-sulfonamide into 1-isopropyl-3-(methoxycarbonylaminosulfonyl)-1H-pyrazole by treatment with dimethyl carbonate or dimethyl pyrocarbonate in the presence of a base:

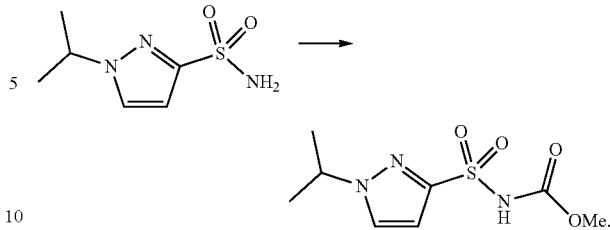

A third aspect of the present invention provides a process of preparing 1,2,3,5,6,7-hexahydro-s-indacen-4-amine:

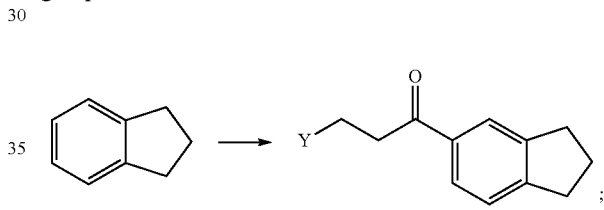

comprising one or more steps selected from:

(i) contacting 2,3-dihydro-1H-indene with YCH$_2$CH$_2$COZ to obtain a substituted 1-(2,3-dihydro-1H-inden-5-yl)propan-1-one, wherein Y and Z are leaving groups:

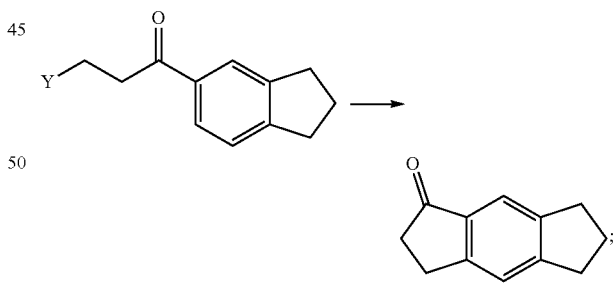

(ii) contacting the substituted 1-(2,3-dihydro-1H-inden-5-yl)propan-1-one with an acid to obtain 1,2,3,5,6,7-hexahydro-s-indacen-1-one:

(iii) converting 1,2,3,5,6,7-hexahydro-s-indacen-1-one into 4-nitro-1,2,3,5,6,7-hexahydro-s-indacen-1-one and/or 8-nitro-1,2,3,5,6,7-hexahydro-s-indacen-1-one:

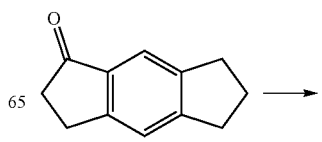

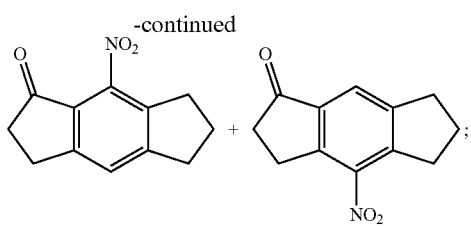

and (iv) reducing 4-nitro-1,2,3,5,6,7-hexahydro-s-indacen-1-one and/or 8-nitro-1,2,3,5,6,7-hexahydro-s-indacen-1-one to obtain 1,2,3,5,6,7-hexahydro-s-indacen-4-amine:

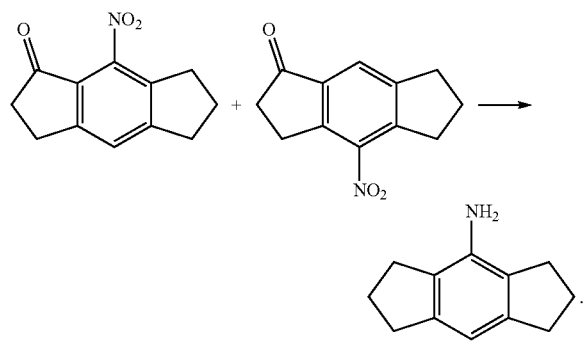

In one embodiment, the process comprises one, two, three or all four of steps (i) to (iv).

Compared to similar prior art processes, the processes of steps (i), (ii), (iii) and (iv) have a reproducibly high yield, are conducted using mild, non-toxic reagents and mild reaction conditions, provide product with excellent HPLC purity, and are therefore suitable for large scale clinical manufacture.

In one embodiment, in step (i), the leaving groups Y and Z are independently selected from fluorine, chlorine, bromine, iodine, toluenesulfonyl, methanesulfonyl and trifluoromethanesulfonyl. Typically, Y and Z are independently selected from chlorine, bromine and iodine. Typically, Y and Z are both chlorine. When both Y and Z are chlorine, 2,3-dihydro-1H-indene is contacted with 3-chloropropionyl chloride to obtain 3-chloro-1-(2,3-dihydro-1H-inden-5-yl)propan-1-one in step (i).

In one embodiment, the reaction of step (i) is carried out in the presence of a catalyst, such as a Lewis acid such as aluminium chloride.

Step (i) may be carried out in the presence of a solvent. In one embodiment, the solvent is a non-polar solvent, such as dichloromethane, chloroform, diethyl ether, n-pentane, n-hexane, n-heptane, toluene, or a mixture thereof. Typically, the solvent is dichloromethane.

In one embodiment, the reaction of step (i) is carried out at a temperature of –20 to 50° C. Typically, the reaction of step (i) is carried out at a temperature of –10 to 40° C.

In one embodiment, in step (ii), the acid is sulfuric acid, hydrochloric acid, or a mixture thereof. Typically, the acid is sulfuric acid. Typically, no additional solvent is used.

In one embodiment, the reaction of step (ii) is carried out at a temperature of 10-90° C. Typically, the reaction of step (ii) is carried out at a temperature of 30-80° C.

In one embodiment, in step (iii), 1,2,3,5,6,7-hexahydro-s-indacen-1-one is converted into 4-nitro-1,2,3,5,6,7-hexahydro-s-indacen-1-one or 8-nitro-1,2,3,5,6,7-hexahydro-s-indacen-1-one or a mixture thereof by treatment with sulfuric acid and nitric acid. Typically, no additional solvent is used.

In one embodiment, the reaction of step (iii) is carried out at a temperature of 0-20° C. Typically, the reaction of step (iii) is carried out at a temperature of 0-10° C.

In one embodiment, the reactions of step (ii) and (iii) are carried out without isolating 1,2,3,5,6,7-hexahydro-s-indacen-1-one.

In one embodiment, the reduction of step (iv) is carried out using a catalyst and hydrogen gas. Typically, the catalyst is a metal catalyst comprising platinum, palladium, rhodium, ruthenium or nickel. Typically, the catalyst is Pd/C, Pd(OH)$_2$, Pt/C, PtO$_2$, platinum black or Raney nickel. More typically, the catalyst is Pd/C or Pd(OH)$_2$. Typically, the hydrogen gas is used at a pressure of 80-120 Psi, typically about 100 Psi. The catalyst and hydrogen gas may be used in the presence of an acid such as sulfuric acid or methanesulfonic acid.

Alternatively, the reduction of step (iv) is carried out using a metal and a source of hydrogen. Typically, the metal is Zn dust or iron. Typically, the source of hydrogen is sulfuric acid, acetic acid, formic acid, ammonium formate or ammonium chloride.

In one embodiment, the reduction of step (iv) is carried out in the presence of a solvent. Typically, the solvent is a polar solvent. Typically, the solvent comprises methanol, ethanol, isopropanol, n-butanol, THF, water, ethyl acetate, acetic acid, or a mixture thereof. Typically, the solvent comprises methanol, ethanol, THF, water, or a mixture thereof.

In one embodiment, the reduction of step (iv) is carried out at a temperature of 10-80° C. Typically, the reduction of step (iv) is carried out at a temperature of 20-60° C.

In one specific embodiment of the third aspect of the present invention, there is provided a process of preparing 1,2,3,5,6,7-hexahydro-s-indacen-4-amine:

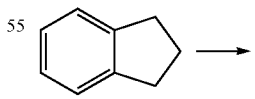

comprising the steps of:

(i) contacting 2,3-dihydro-1H-indene with 3-chloropropionyl chloride in the presence of a Lewis acid to obtain 3-chloro-1-(2,3-dihydro-1H-inden-5-yl)propan-1-one:

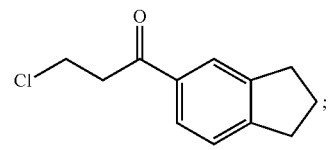

(ii) contacting 3-chloro-1-(2,3-dihydro-1H-inden-5-yl)propan-1-one with an acid to obtain 1,2,3,5,6,7-hexahydro-s-indacen-1-one:

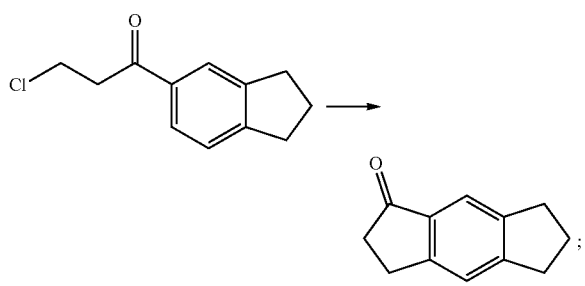

(iii) converting 1,2,3,5,6,7-hexahydro-s-indacen-1-one into 4-nitro-1,2,3,5,6,7-hexahydro-s-indacen-1-one and/or 8-nitro-1,2,3,5,6,7-hexahydro-s-indacen-1-one by treatment with sulfuric acid and nitric acid:

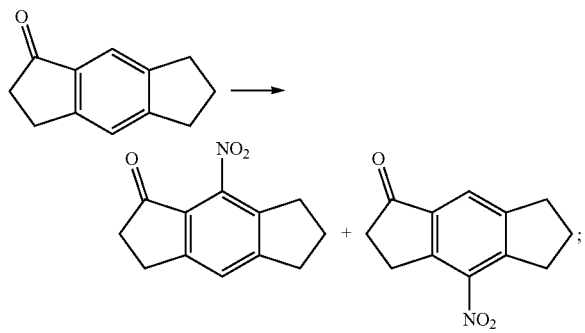

and (iv) reducing 4-nitro-1,2,3,5,6,7-hexahydro-s-indacen-1-one and/or 8-nitro-1,2,3,5,6,7-hexahydro-s-indacen-1-one to obtain 1,2,3,5,6,7-hexahydro-s-indacen-4-amine:

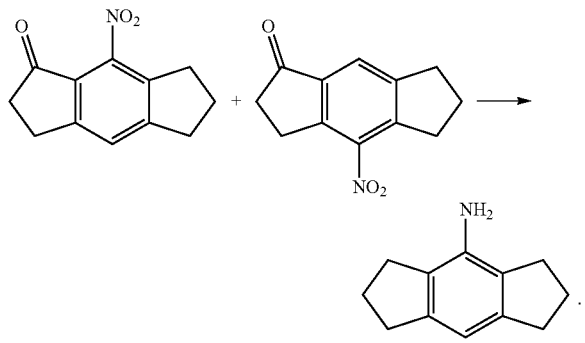

A fourth aspect of the present invention provides N-((1,2,3,5,6,7-hexahydro-s-indacen-4-yl)carbamoyl)-1-isopropyl-1H-pyrazole-3-sulfonamide or a salt thereof obtainable or obtained by a process of the first, second or third aspect of the invention.

Typically, the N-((1,2,3,5,6,7-hexahydro-s-indacen-4-yl)carbamoyl)-1-isopropyl-1H-pyrazole-3-sulfonamide or the salt thereof has a HPLC purity of 98% or more, or 98.5% or more, or 98.6% or more, or 98.7% or more, or 98.8% or more, or 98.9% or more, or 99% or more, or 99.1% or more, or 99.2% or more, or 99.3% or more.

N-((1,2,3,5,6,7-Hexahydro-s-indacen-4-yl)carbamoyl)-1-isopropyl-1H-pyrazole-3-sulfonamide can be used both, in its free acid form and in its salt form. Salts may be formed with suitable cations, including but not limited to lithium, sodium, potassium, magnesium, calcium and ammonium. The salt may be a mono- or di-salt. Preferably the salt is a mono- or di-lithium, sodium, potassium, magnesium, calcium or ammonium salt. Preferably the salt is a mono- or di-sodium salt or a mono- or di-potassium salt. More preferably the salt is a mono-sodium mono-hydrate salt.

Preferably any salt is a pharmaceutically acceptable non-toxic salt. However, in addition to pharmaceutically acceptable salts, other salts are included in the present invention, since they have potential to serve as intermediates in the purification or preparation of other, for example, pharmaceutically acceptable salts, or are useful for identification, characterisation or purification of the free acid.

N-((1,2,3,5,6,7-Hexahydro-s-indacen-4-yl)carbamoyl)-1-isopropyl-1H-pyrazole-3-sulfonamide and salts thereof may be anhydrous or in the form of a hydrate (e.g. a hemihydrate, monohydrate, dihydrate or trihydrate) or other solvate. Such other solvates may be formed with common organic solvents, including but not limited to, alcoholic solvents e.g. methanol, ethanol or isopropanol.

N-((1,2,3,5,6,7-Hexahydro-s-indacen-4-yl)carbamoyl)-1-isopropyl-1H-pyrazole-3-sulfonamide and salts thereof may contain any stable isotope including, but not limited to $^{12}C$, $^{13}C$, $^{1}H$, $^{2}H$ (D), $^{14}N$, $^{15}N$, $^{16}O$, $^{17}O$ and $^{18}O$, and any radioisotope including, but not limited to $^{11}C$, $^{14}C$, $^{3}H$ (T), $^{13}N$ and $^{15}O$.

N-((1,2,3,5,6,7-Hexahydro-s-indacen-4-yl)carbamoyl)-1-isopropyl-1H-pyrazole-3-sulfonamide and salts thereof may be in any polymorphic or amorphous form.

A fifth aspect of the present invention provides a pharmaceutical composition comprising N-((1,2,3,5,6,7-hexahydro-s-indacen-4-yl)carbamoyl)-1-isopropyl-1H-pyrazole-3-sulfonamide or a salt thereof, and a pharmaceutically acceptable excipient.

Conventional procedures for the selection and preparation of suitable pharmaceutical formulations are described in, for example, "Aulton's Pharmaceutics—The Design and Manufacture of Medicines", M. E. Aulton and K. M. G. Taylor, Churchill Livingstone Elsevier, 4$^{th}$ Ed., 2013. Pharmaceutically acceptable excipients including adjuvants, diluents or carriers that may be used in the pharmaceutical compositions of the invention, are those conventionally employed in the field of pharmaceutical formulation.

A sixth aspect of the present invention provides the compound of the fourth aspect of the invention, or a pharmaceutical composition of the fifth aspect of the invention, for use in medicine, and/or for use in the treatment or prevention of a disease, disorder or condition.

Co-pending and commonly owned patent applications PCT/EP2018/072111, PCT/EP2018/072115, PCT/EP2018/072119, PCT/EP2018/072123, PCT/EP2018/072125, PCT/EP2018/072133, and PCT/EP2018/072134, all of which are hereby incorporated by reference, disclose the use of sulfonylureas such as the compound of the fourth aspect of the invention in the treatment and prevention of diseases, disorders and conditions, most especially by NLRP3 inhibition. The diseases, disorders and conditions mentioned in these co-pending and commonly owned patent applications are hereby incorporated by reference.

In one embodiment, the disease, disorder or condition to be treated or prevented is selected from:
(i) inflammation;
(ii) an auto-immune disease;
(iii) cancer;
(iv) an infection;
(v) a central nervous system disease;

(vi) a metabolic disease;
(vii) a cardiovascular disease;
(viii) a respiratory disease;
(ix) a liver disease;
(x) a renal disease;
(xi) an ocular disease;
(xii) a skin disease;
(xiii) a lymphatic condition;
(xiv) a psychological disorder;
(xv) graft versus host disease;
(xvi) allodynia;
(xvii) a condition associated with diabetes; and
(xviii) any disease where an individual has been determined to carry a germline or somatic non-silent mutation in NLRP3.

In another embodiment, the disease, disorder or condition to be treated or prevented is selected from:
(i) cryopyrin-associated periodic syndromes (CAPS);
(ii) Muckle-Wells syndrome (MWS);
(iii) familial cold autoinflammatory syndrome (FCAS);
(iv) neonatal onset multisystem inflammatory disease (NOMID);
(v) familial Mediterranean fever (FMF);
(vi) pyogenic arthritis, pyoderma gangrenosum and acne syndrome (PAPA);
(vii) hyperimmunoglobulinaemia D and periodic fever syndrome (HIDS);
(viii) Tumour Necrosis Factor (TNF) Receptor-Associated Periodic Syndrome (TRAPS);
(ix) systemic juvenile idiopathic arthritis;
(x) adult-onset Still's disease (AOSD);
(xi) relapsing polychondritis;
(xii) Schnitzler's syndrome;
(xiii) Sweet's syndrome;
(xiv) Behcet's disease;
(xv) anti-synthetase syndrome;
(xvi) deficiency of interleukin 1 receptor antagonist (DIRA); and
(xvii) haploinsufficiency of A20 (HA20).

Typically, the treatment or prevention of the disease, disorder or condition comprises the administration of the compound of the fourth aspect of the invention or the pharmaceutical composition of the fifth aspect of the invention to a subject.

Any of the pharmaceutical compositions employed in the present invention can be administered by oral, parenteral (including intravenous, subcutaneous, intramuscular, intradermal, intratracheal, intraperitoneal, intraarticular, intracranial and epidural), airway (aerosol), rectal, vaginal, ocular or topical (including transdermal, buccal, mucosal, sublingual and topical ocular) administration.

Typically, the mode of administration selected is that most appropriate to the disorder, disease or condition to be treated or prevented.

The dose of the compound of the fourth aspect of the invention will, of course, vary with the disorder, disease or condition to be treated or prevented. In general, a suitable dose will be in the range of 0.01 to 500 mg per kilogram body weight of the recipient per day. The desired dose may be presented at an appropriate interval such as once every other day, once a day, twice a day, three times a day or four times a day. The desired dose may be administered in unit dosage form, for example, containing 1 mg to 50 g of active ingredient per unit dosage form.

A seventh aspect of the invention provides a method of inhibiting NLRP3, the method comprising the use of the compound of the fourth aspect of the invention or the pharmaceutical composition of the fifth aspect of the invention, to inhibit NLRP3.

For the avoidance of doubt, insofar as is practicable any embodiment of a given aspect of the present invention may occur in combination with any other embodiment of the same aspect of the present invention. In addition, insofar as is practicable it is to be understood that any preferred, typical or optional embodiment of any aspect of the present invention should also be considered as a preferred, typical or optional embodiment of any other aspect of the present invention.

EXAMPLES

All solvents, reagents and compounds were purchased and used without further purification unless stated otherwise.

Abbreviations

DCM dichloromethane
DMF N,N-dimethylformamide
DMSO dimethyl sulfoxide
eq equivalents
HMPA hexamethylphosphoramide
iPr isopropyl
MTBE methyl tert-butyl ether
Pd/C palladium on carbon
10% Pd/C 10% Pd w/w adsorbed on carbon
5% Pd/C 5% Pd w/w adsorbed on carbon
prep-HPLC preparative high performance liquid chromatography
THF tetrahydrofuran
vol volumes
Experimental Methods
NMR Methods:
NMR spectra were run at 293-298 K on one of the following spectrometers: an Agilent 500 MHz, 400 MHz or 300 MHz spectrometer, a Bruker BioSpin AG 400 MHz spectrometer, a Bruker 500 MHz spectrometer, or a Varian 400 MHz spectrometer using VNMRJ.
LC-MS Methods:
Reaction scheme 1 (steps a-c) and reaction scheme 2 (steps i-iv (method A)): Using Waters-Acquity UPLC system with PDA detector and SQD mass detector.
Reaction scheme 1 (steps d-e) and reaction scheme 3: Using Agilent 1260 Infinity II (liquid chromatography) 6125B MSD Single Quadrupol with API electrospray source (mass spectrometry).
Reaction scheme 2 (steps i-iv (methods B and C)): Using UPLC-Waters, Quatropremier XE-Waters. Mobile phase A: 0.1% formic acid in water. Mobile phase B: 0.1% formic acid in acetonitrile.
HPLC Methods:
Reaction scheme 1 (steps a-c) and reaction scheme 2 (steps i-iv (method A)): Reversed phase chromatography was carried out using waters Alliance HPLC system with PDA detector.
Reaction scheme 1 (steps d-e) and reaction scheme 3: Using Agilent 1260 Infinity II.
Reaction scheme 2 (steps i-iv (methods B and C)): Reversed phase chromatography was carried out using Waters e-2695 series with 2998 PDA detector. Mobile Phase A: 0.01 M ammonium acetate in water; Mobile Phase B: acetonitrile; Column: X-Bridge C18 (150 mm×4.6 mm, 3.5 micron).

SYNTHESIS EXAMPLES

1-Isopropyl-3-(methoxycarbonylaminosulfonyl)-1H-pyrazole (6)

1-Isopropyl-3-(methoxycarbonylaminosulfonyl)-1H-pyrazole (6) was prepared according to the reaction sequence illustrated in Reaction Scheme 1.

Reaction Scheme 1

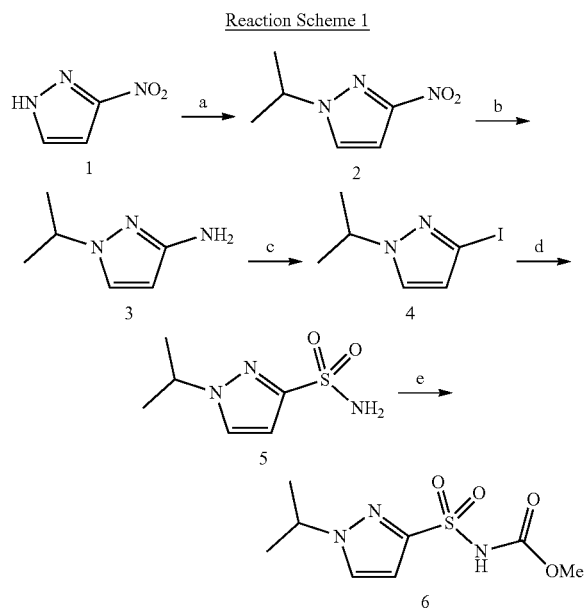

Reaction Scheme 1 - Step a

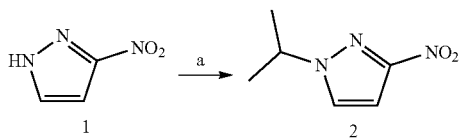

A 1.0 kilolitre clean and dry reactor was charged with acetonitrile (155 L) and 3-nitro-1H-pyrazole (1) (15.50 Kg) at 25-30° C. Potassium carbonate (37.88 Kg) and 2-iodo-propane (24.46 Kg) were added to the reaction mixture at 25-30° C. Then the temperature was raised to 40-45° C. and maintained at 40-45° C. for 24 hours. Then further 2-iodo-propane (2.33 Kg) was added to the reaction mixture at 40-45° C. and the reaction mixture was maintained at 40-45° C. for 96 hours. Then further 2-iodo-propane (3.49 Kg) and potassium carbonate (3.78 Kg) were added to the reaction mixture at 40-45° C. Then the temperature was raised to 60-65° C. and maintained at 60-65° C. for 16 hours.

The absence of 3-nitro-1H-pyrazole (1) was confirmed by HPLC (Limit: NMT 1.0%). If, for a given run, the reaction mixture did not comply with the HPLC limit, it was maintained at 60-65° C. under stirring until the desired HPLC purity was achieved.

After completion of the reaction, 80-90% of the solvent was distilled off under vacuum at below 45° C. A mixture of acetonitrile (31 L) and MTBE (124 L) (2:8) was charged to the reaction mixture and the reaction mixture was stirred for 30 minutes at 25-30° C. The resulting salts were filtered and washed with a mixture of acetonitrile (15.5 L) and MTBE (62 L) (2:8) at 25-30° C. The filtrate was distilled off completely at 45° C. The resultant crude product was co-distilled with MTBE (15.5 L) at 45° C. and allowed to stand for 12 hours to afford solid crystals. The crystals were charged with heptane (124 L) and stirred for 1-2 hours at 25-30° C. The reaction mixture was filtered, washed with heptane (31 L) at 25-30° C., and dried in an air oven at 25-30° C. for 4-5 hours to afford the product.

Final Product: 1-isopropyl-3-nitro-1H-pyrazole (2)

Off white solid
Output: 14.5 Kg
Yield: 68.2%
Melting point: 45-48° C.
1H NMR (DMSO-d6; 400 MHz): 1.45 (d, 6H), 4.65 (sept, 1H), 7.06 (s, 1H), and 8.12 (s, 1H).
MS: (M+H$^+$)=156.10
Moisture content (by Karl Fischer titration): ≤1.0%
HPLC purity: 98.61%
HPLC [X-bridge C18 column, 4.6×150 mm, 3.5 μm, mobile phase A=10 mM ammonium bicarbonate in water, mobile phase B=acetonitrile, gradient programme (time/% B)=0/10, 7/90, 15/90, 15.01/10; flow rate 1 mL per minute, temp=25° C.): $R_t$=6.11 minutes]

Reaction Scheme 1 - Step b

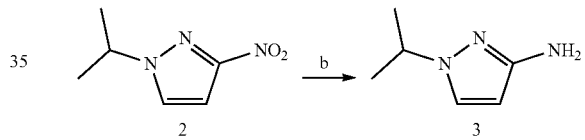

A 0.5 kilolitre clean and dry pressure reactor was charged with 1-isopropyl-3-nitro-1H-pyrazole (2) (14.5 Kg) at 25-30° C. Methanol (130.5 L) was charged at 25-30° C. under a nitrogen atmosphere. The reaction mixture was stirred for 30 minutes at 25-30° C. Then 5% Pd/C (4.35 Kg) (50% wet) suspended in methanol (14.5 L) was charged at 25-30° C. under nitrogen. The reaction mixture was degassed under vacuum and filled with an argon atmosphere (50 Psi) three times. The reaction mixture was degassed under vacuum and filled with a hydrogen atmosphere (50 Psi) three times. Then the reaction mixture was stirred under hydrogen pressure (100 Psi) at room temperature for 14 hours. The temperature was gradually raised up to 55° C.

The absence of 1-isopropyl-3-nitro-1H-pyrazole (2) was confirmed by HPLC (Limit: NMT 1.0%). If, for a given run, the reaction mixture did not comply with the HPLC limit, it was maintained at room temperature under stirring until the desired HPLC purity was achieved.

After completion of the reaction, the reaction mixture was cooled to 25-30° C. The reaction mixture was degassed under vacuum and filled with a nitrogen atmosphere three times. The reaction mixture was filtered through a candy nutch filter, followed by a micro filter and the bed was washed with methanol (29.0 L). 90-95% of the solvent was distilled off under vacuum at below 40-45° C. and the resultant mixture was co-distilled with acetonitrile at below 40-45° C. to afford the product.

Final Product: 1-isopropyl-3-amino-1H-pyrazole (3)

Greenish black liquid
Output: 11.5 Kg
Yield: 98.54%
1H NMR (DMSO-d6; 400 MHz): 1.35 (d, 6H), 4.18 (sept, 1H), 4.45 (br s, 2H), 5.37 (s, 1H), and 7.28 (s, 1H).
MS: (M+H$^+$)=126.17
HPLC purity: 98.61%
HPLC [X-bridge C18 column, 4.6×150 mm, 3.5 μm, mobile phase A=10 mM ammonium bicarbonate in water, mobile phase B=acetonitrile, gradient programme (time/% B)=0/10, 7/90, 15/90, 15.01/10; flow rate 1 mL per minute, temp=25° C.): R$_t$=3.84 minutes]

Reaction Scheme 1 - Step c

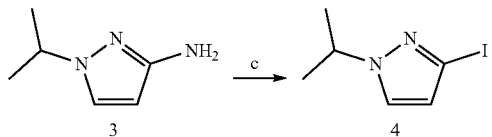

A 1.0 kilolitre clean reactor was charged with 1-isopropyl-3-amino-1H-pyrazole (3) (12.20 Kg) at 25-30° C. Water (122 L) and acetonitrile (61 L) were charged at 25-30° C. and the reaction mixture was stirred for 10 minutes. Then the reaction mixture was cooled to −5 to 0° C. Sulfuric acid solution*[1] was added slowly to the reaction mixture at −5 to 0° C. The resulting reaction mixture was maintained for 30 minutes at −5 to 0° C. Then sodium nitrite solution*[2] was added slowly to the reaction mixture at −5 to 0° C.

The resulting reaction mixture was maintained for 30-35 minutes at −5 to 0° C. to form a diazonium solution.

A 1.0 kilolitre clean reactor was charged with potassium iodide (48.61 Kg) and water (122 L) at 25-30° C. The reaction mixture was cooled to −5 to 0° C. The diazonium solution obtained earlier was added slowly to the pre-cooled potassium iodide solution at −5 to 0° C. The resulting reaction mixture was maintained for 30 minutes at −5 to 0° C.

The absence of 1-isopropyl-3-amino-1H-pyrazole (3) was confirmed by HPLC (Limit: NMT 1.0%). If, for a given run, the reaction mixture did not comply with the HPLC limit, it was maintained at room temperature under stirring until the desired HPLC purity was achieved.

After completion of the reaction, solid sodium thiosulfate (6.0 Kg) was charged to the reaction mixture at −5 to 0° C. Then the pH of the reaction mixture was adjusted to 6-7 using 1.25 N sodium hydroxide solution*[3] at 10-15° C. MTBE (122 L) was charged to the reaction mixture at 25-30° C. and the reaction mixture was stirred at 25-30° C. for 30 minutes. The layers were separated and the organic layer was kept aside. MTBE (61 L) was charged to the aqueous layer at 25-30° C. The reaction mixture was stirred at 25-30° C. for 30 minutes and allowed to settle at 25-30° C. for 30 minutes. The layers were separated. The first portion of a sodium thiosulfate solution*[4] was charged to the combined organic layers at 25-30° C. and the reaction mixture was stirred at 25-30° C. for 30 minutes. The layers were separated. Then the second portion of the sodium thiosulfate solution*[4] was charged to the organic layer at 25-30° C. and the reaction mixture was stirred at 25-30° C. for 30 minutes. The layers were separated. A brine solution was charged to the organic layer at 25-30° C. and the reaction mixture was stirred at 25-30° C. for 30 minutes. The layers were separated. The organic layer was dried over anhydrous Na$_2$SO$_4$ and the solvent was distilled completely under vacuum at below 40-45° C. The crude product obtained was purified by high vacuum distillation by charging into a clean and dry 20 L 4-neck round bottom flask equipped with Vigreux column, T-bend, condenser, cow joint and three receiver single-neck round bottom flasks at 25-30° C. Vacuum was applied at 720-740 mmHg and the bath temperature was raised to 85-90° C. A first fraction was collected at a vapour temperature of 24-90° C. Then the bath temperature was raised to 90-122° C. A second fraction (1-isopropyl-3-iodo-1H-pyrazole (4); 12.03 Kg; HPLC purity 99.28%) was collected at a vapour temperature of 95-102° C. A third fraction (1-isopropyl-3-iodo-1H-pyrazole (4); 6.0 Kg; HPLC purity 95%) was collected at a vapour temperature of 95-104° C. The third fraction (6.0 Kg) was redistilled and a pure fraction was collected at a vapour temperature of 95-102° C. (1-isopropyl-3-iodo-1H-pyrazole (4); 5.3 Kg; HPLC purity 99.28%).

1: To prepare the sulfuric acid solution, sulfuric acid (10.45 Kg) was added slowly to water (61 L) at 10-15° C.

2: To prepare the sodium nitrite solution, sodium nitrite (7.27 Kg) solid was added slowly to water (61 L) at 25-30° C. (endothermic reaction).

3: To prepare the sodium hydroxide solution, sodium hydroxide (6.1 Kg) was added slowly to water (122 L) at 25-30° C.

4: To prepare the sodium thiosulfate solution, sodium thiosulfate (6 Kg) was added slowly to water (122 L) at 25-30° C. and the prepared solution was divided into two portions.

Final Product: 1-isopropyl-3-iodo-1H-pyrazole (4)

Pale yellow liquid
Output: 12.03 Kg (batch 1)+5.3 Kg (batch 2)=17.33 Kg
Overall Yield (combination of batch 1 and batch 2): 75.34% 1H NMR (CDCl$_3$; 500 MHz): 1.50 (d, 6H), 4.51 (sept, 1H), 6.39 (s, 1H), and 7.25 (s, 1H).
MS: (M+H$^+$)=236.06
HPLC purity: 99.28%
HPLC [X-bridge C18 column, 4.6×150 mm, 3.5 μm, mobile phase A=10 mM ammonium bicarbonate in water, mobile phase B=acetonitrile, gradient programme (time/% B)=0/10, 7/90, 15/90, 15.01/10; flow rate 1 mL per minute, temp=25° C.):
R$_t$=6.98 minutes]

Reaction Scheme 1 - Step d

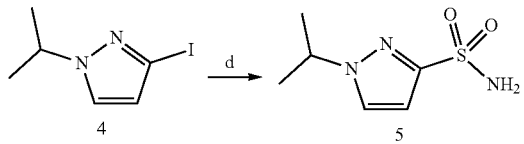

1-Isopropyl-3-iodo-1H-pyrazole (4) (250.0 g, 1 eq) was placed in 2-MeTHF (6.75 vol, 1688 mL) and n-heptane (3 vol, 750 mL) and cooled to 10° C. A solution of iPrMgCl (1.1 eq, 2 M in THF, 598 g) was added slowly over 35 minutes. After 60 minutes at 10° C., an IPC (in process control) was drawn and conversion was monitored by HPLC (100% conversion).

The reactor was slightly evacuated (700-800 mbar) and the addition of SO$_2$ gas above the surface was started (exotherm). After SO$_2$ (77 g, 1.14 eq) had been added over 79 minutes, the reaction turned yellow and the addition of SO$_2$ gas was stopped. The reaction was rendered inert and an IPC showed 99.32% conversion (measured by HPLC).

Water (5 vol, 1250 mL) was added slowly at 10° C. and the reaction mixture was warmed up to 20° C. The layers were separated and the colourless organic layer was back-extracted with water (2 vol, 500 mL). The aqueous layers were combined and tri-sodium citrate (1.75 eq, 545 g) was added. The reaction mixture was cooled to 10° C. Hydroxylamine-O-sulfonic acid (1.5 eq, 180 g) was dissolved in water (1 vol, 250 mL) and the solution was added slowly to the reaction mixture over 31 minutes (exotherm). The reaction mixture was warmed to 20° C. and stirred for 40 minutes. An IPC showed 98.87% conversion (measured by HPLC).

2-MeTHF (7.5 vol, 1880 mL) was added and the layers were separated. The aqueous layer was back-extracted with 2-MeTHF (4 vol, 1000 mL). The combined organic layers were filtered over Na$_2$SO$_4$ (3 weight eq, 750 g) and the filter-cake was washed with 2-MeTHF (4 vol, 1000 mL). The combined filtrates were concentrated in vacuo to 3.5 residual vol (875 mL) and cooled to room temperature. As no crystallization occurred, a sample of the concentrate (1 mL) was diluted with n-heptane (1 mL). After crystallization of the sample occurred, the sample was added back to the reaction mixture. Stirring was continued at 20° C. for 30 minutes before the suspension was warmed to 30° C. n-Heptane (6 vol, 1500 mL) was added slowly over 80 minutes at 30° C. and the reaction mixture was stirred for another 60 minutes at 30° C. The suspension was cooled to 20° C. over 60 minutes and kept at 20° C. overnight. Then the suspension was filtered, rinsing with mother liquor, then with 2-MeTHF/n-heptane (1:2, 3 vol, 750 mL) and n-heptane (2 vol, 500 mL). The filter-cake was dried in vacuo to afford the product.

Final Product: 1-isopropyl-1H-pyrazole-3-sulfonamide (5)

Brown-yellow solid
Output: 186.6 g
Yield: 93.1%
1H NMR (DMSO-d6; 400 MHz): 7.92 (d, J=2.28 Hz, 1H), 7.39 (s, 2H), 6.57 (d, J=2.28 Hz, 1H), 4.57 (sept, J=6.67 Hz, 1H), and 1.43 (d, J=6.59 Hz, 6H).
Dry-matter content: 99.24% w/w
HPLC purity: 99.71%

1-Isopropyl-1H-pyrazole-3-sulfonamide (5) (1 eq, 10.0 g) was suspended in dimethyl carbonate (6 vol, 60 mL) and a solution of NaOMe in methanol (30%, 1.75 eq, 16.66 g) was added. The reaction mixture was heated to 65° C. overnight and then reduced in vacuo at 45° C. by 2 volumes (20 mL) of solvent. The reaction mixture was cooled to room temperature and water (3.25 vol, 32.5 mL) was added slowly. The reaction mixture was further concentrated in vacuo at 45° C. by 2 volumes (20 mL) of solvent. n-Heptane (5 vol, 50 mL) was added at 20° C., followed by 32% aqueous hydrochloric acid solution (1.9 eq, 11.7 g), added slowly over 37 minutes. The suspension was stirred at 20° C. for 20 minutes and then further diluted with n-heptane (2 vol, 20 mL) and stirred for another 20 minutes. The resulting suspension was filtered, rinsing with mother liquor, then washed with water (5 vol, 50 mL), n-heptane (5 vol, 50 mL), a mixture of 2-MeTHF/n-heptane (1:2, 4.5 vol, 45 mL) and n-heptane (2 vol, 20 mL). The filter-cake was dried in vacuo to afford the product.

Final Product: 1-isopropyl-3-(methoxycarbonylaminosulfonyl)-1H-pyrazole (6)

White solid
Output: 12.0 g
Yield: 91.9%
1H NMR (DMSO-d6; 400 MHz): 12.09 (br s, 1H), 8.01 (d, J=2.28 Hz, 1H), 6.76 (d, J=2.28 Hz, 1H), 4.61 (sept, J=6.67 Hz, 1H), 3.59 (s, 3H), and 1.43 (d, J=6.59 Hz, 6H).
Dry-matter content: 99.12% w/w
HPLC purity: 99.69%

1,2,3,5,6,7-Hexahydro-s-indacen-4-amine (16)

1,2,3,5,6,7-Hexahydro-s-indacen-4-amine (16) was prepared according to the reaction sequence illustrated in Reaction Scheme 2.

Reaction Scheme 1 - Step e

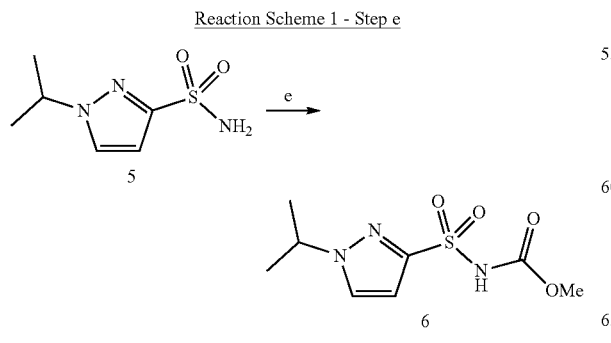

Reaction Scheme 2

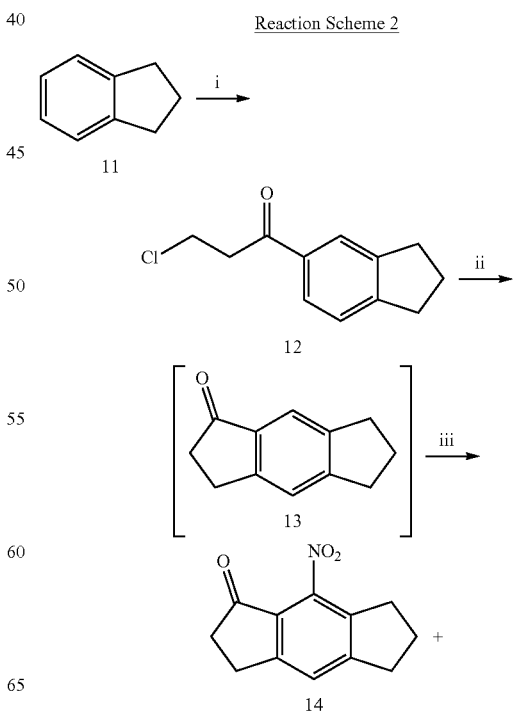

21
-continued

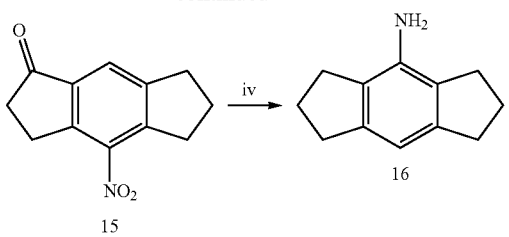

Reaction Scheme 2 - Step i (Method A)

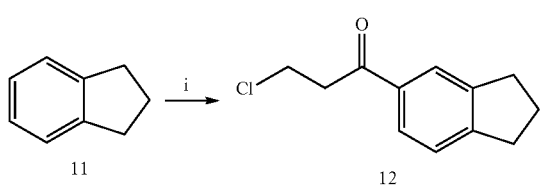

DCM (440 L) and AlCl₃ (57.08 Kg) were charged at 25-30° C. under a nitrogen atmosphere into a 500 L clean and dry glass-lined reactor. A solution of 3-chloropropanoyl chloride (51.99 Kg) in DCM (44 L) was added slowly at −10 to −5° C. under a nitrogen atmosphere. The reaction mixture was maintained for 30 minutes at −10° C. under a nitrogen atmosphere. Then a solution of indane (11) (44.00 Kg) in DCM (44 L) was added slowly to the reaction mixture at −10 to −5° C. and the reaction mixture was maintained for 16 hours at 10-15° C. The absence of indane (11) was confirmed by HPLC (Limit: ≤5.0%).

After completion of the reaction, the reaction mixture was added slowly to a 3 N hydrochloric acid solution (prepared from water (330 L) and conc. hydrochloric acid (110 L)) at 0-10° C. The reaction mixture was stirred at 25-30° C. for 30 minutes and allowed to settle at 25-30° C. for 30 minutes. The layers were separated and the organic layer (OL-1) was kept aside. DCM (220 L) was charged to the aqueous layer at 25-30° C. The reaction mixture was stirred at 25-30° C. for 30 minutes and allowed to settle at 25-30° C. for 30 minutes. The layers were separated (aqueous layer and organic layer (OL-2). 10% Saturated sodium bicarbonate solution (prepared from water (880 L) and sodium bicarbonate (88.00 Kg)) was charged to the combined organic layers (OL-1 and OL-2) at 25-30° C. The reaction mixture was stirred at 25-30° C. for 30 minutes and allowed to settle at 25-30° C. for 30 minutes. The layers were separated. A brine solution (prepared from water (220 L) and sodium chloride (84.48 Kg)) was charged to the organic layer at 25-30° C. The reaction mixture was stirred at 25-30° C. for 30 minutes and allowed to settle at 25-30° C. for 30 minutes. The layers were separated. The organic layer was dried over anhydrous Na₂SO₄. The solvent was distilled under vacuum at 35-40° C. until 5% remained. n-Hexane (88 L) was charged to the reaction mixture and the solvent was distilled completely at 35-40° C. until no condensate drops were formed. n-Hexane (88 L) was charged to the reaction mixture and the reaction mixture was cooled to 5-10° C. and maintained at 5-10° C. for 30 minutes. The solid product was filtered, washed with cooled hexane (44 L), and dried in a hot air oven at 40-45° C. for 6 hours to afford the product.

22
Final Product: 3-chloro-1-(2,3-dihydro-1H-inden-5-yl)propan-1-one (12)

Off white solid
Output: 50.8 Kg
Yield: 65.59%
1H NMR (CDCl₃; 500 MHz): 7.81 (s, 1H), 7.75 (d, J=8.0 Hz, 1H), 7.31 (d, J=8.0 Hz, 1H), 3.93 (t, J=7.0 Hz, 2H), 3.45 (t, J=7.0 Hz, 2H), 2.97, (t, J=7.50 Hz, 4H), and 2.15-2.09 (m, 2H).
Moisture content (by Karl Fischer titration): ≤0.5%
HPLC purity: 99.57%

Reaction Scheme 2-Steps ii and iii (Method A)

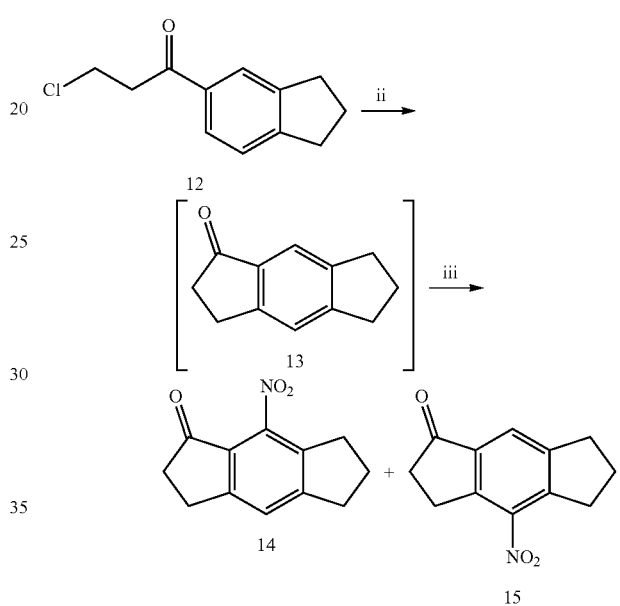

Sulfuric acid (255.0 L) was charged at 25-30° C. into a 500 L clean and dry glass-lined reactor. Then 3-chloro-1-(2,3-dihydro-1H-inden-5-yl)propan-1-one (12) (51.00 Kg) was charged lot wise at 25-30° C. The reaction mixture was maintained for 30 minutes at 25-30° C. Then the reaction mixture was slowly heated to 55-60° C. and maintained at 55-60° C. for 48 hours. The absence of 3-chloro-1-(2,3-dihydro-1H-inden-5-yl)propan-1-one (12) was confirmed by HPLC (Limit: ≤1.0%).

Then the reaction mixture was cooled to 0-5° C. A nitration mixture*⁵ was added slowly at 0-5° C. and the reaction mixture was maintained at 0-5° C. for 1 hour. The absence of 1,2,3,5,6,7-hexahydro-s-indacen-1-one (13) was confirmed by HPLC (Limit: ≤1.0%).

After completion of the reaction, the reaction mixture was added slowly to water (1275 L) at 0-10° C. The solid crude product was filtered, taken in water (510 L) and stirred for 30 minutes at 25-30° C. The solid crude product was filtered, washed with water (255 L), taken in methanol (102 L), cooled to 0-5° C., and maintained at 0-5° C. for 30 minutes. The solid crude product was filtered, washed with cold methanol (51 L), and dried in a hot air oven at 40-45° C. for 6 hours. The moisture content of the solid crude product was confirmed by Karl Fischer titration as 0.5%.

The solid crude product (42.5 Kg) and DCM (510 L) were charged at 25-30° C. into a 1.0 kilolitre clean and dry reactor. Water (408 L) at 25-30° C. was added slowly and stirred for 30 minutes. The crude product was filtered through a bed of Celite® (prepared from Celite® (12.75 Kg) and DCM (51 L)) and the bed was washed with DCM (51 L). The layers were separated. To the organic layer was charged a brine solution (prepared from water (255 L) and sodium chloride (51.0 Kg)) at 25-30° C. The reaction mixture was stirred at 25-30° C. for 30 minutes and allowed to settle at 25-30° C. for 30 minutes. The layers were separated. The organic layer was dried over anhydrous $Na_2SO_4$ (51.0 Kg). The solvent was distilled under vacuum at below 35-40° C. until 5% remained. Methanol (51 L) was charged to the reaction mixture at 35-40° C. and distilled at 40-45° C. Methanol (102 L) was charged to the reaction mixture at 35-40° C., cooled to 0-5° C. and maintained for 30 minutes. The solid product was filtered, washed with cooled methanol (25.5 L), and dried in a hot air oven at 40-45° C. for 6 hours to afford the product.

5: To prepare the nitration mixture, sulfuric acid (16.83 L) was charged at 25-30° C. into a 160 L clean and dry glass-lined reactor. The reaction mixture was cooled to 0-5° C. Nitric acid (16.83 L) at 0-5° C. was added slowly and the reaction mixture was maintained for 30 minutes at 0-5° C. to afford the nitration mixture.

Final Product: 8-nitro-1,2,3,5,6,7-hexahydro-s-indacen-1-one (14) and 4-nitro-1,2,3,5,6,7-hexahydro-s-indacen-1-one (15)

Pale brown solid
Weight ratio of 14:15 was 9.6:1.
Combined Output (14+15): 31.40 Kg
Combined Yield (14+15): 59.2%
1H NMR ($CDCl_3$; 400 MHz): 7.45 (s, 1H), 3.13-3.06 (m, 2H), 3.08-2.97 (m, 4H), 2.82-2.76 (m, 2H), and 2.25-2.16 (m, 2H).
Moisture content (by Karl Fischer titration): ≤0.5%
HPLC purity: 91.61%

Reaction Scheme 2-Step iv (Method A)

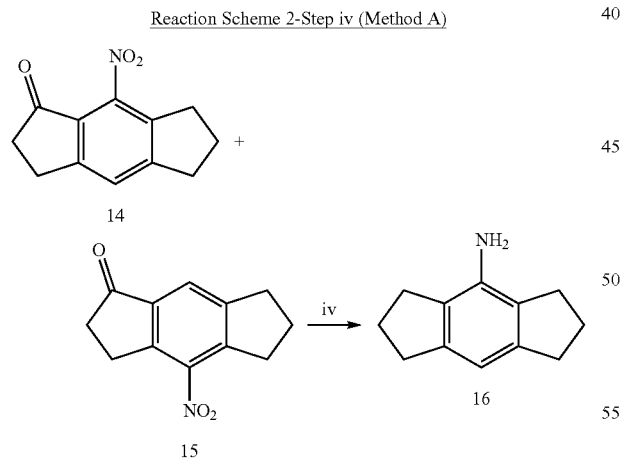

A mixture of 8-nitro-1,2,3,5,6,7-hexahydro-s-indacen-1-one (14) and 4-nitro-1,2,3,5,6,7-hexahydro-s-indacen-1-one (15) (17.00 Kg) at 25-30° C. was charged into a 600 L clean and dry pressure reactor. Methanol (170 L) was charged at 25-30° C. THF (85 L) was charged at 25-30° C. Methane sulfonic acid (8.272 Kg) was slowly charged at 25-30° C. 20% Pd(OH)₂ solution*⁶ was charged and the reaction mixture was maintained for 30 minutes. The reaction mixture was degassed under vacuum and filled with an argon atmosphere (50 Psi) three times. The reaction mixture was degassed under vacuum and filled with a hydrogen atmosphere (50 Psi) three times. Then the reaction mixture was stirred under hydrogen pressure (100 Psi) at room temperature for 24 hours. The temperature was gradually raised up to 55° C. The absence of 8-nitro-1,2,3,5,6,7-hexahydro-s-indacen-1-one (14) and 4-nitro-1,2,3,5,6,7-hexahydro-s-indacen-1-one (15) was confirmed by HPLC (Limit: ≤1.0%).

After completion of the reaction, the reaction mixture was cooled to 25-30° C. The reaction mixture was filtered through a candy nutch filter, followed by a micro filter and the bed was washed with methanol (34 L). 95% of the solvent was distilled off under vacuum at below 45-50° C. Water (85 L) was charged into the reaction mixture at 25-30° C. and maintained for 30 minutes. The reaction mixture was cooled to 5-10° C. The pH was adjusted to about 9-10 with 2 N aqueous NaOH solution (prepared from NaOH (4.08 Kg) and water (51 L)) and the reaction mixture was stirred for 30 minutes. Then DCM (85 L) was charged to the reaction mixture and the reaction mixture was stirred for 30 minutes. The reaction mixture was stirred for a further 30 minutes, whilst bringing the temperature up to 25-30° C. The reaction mixture was allowed to settle for 30 minutes, whilst the temperature was maintained at 25-30° C. The layers were separated and the organic layer (OL-1) was kept aside. DCM (34 L) was charged to the aqueous layer at 25-30° C. The reaction mixture was stirred at 25-30° C. for 30 minutes and allowed to settle at 25-30° C. for 30 minutes. The layers were separated into the aqueous layer and organic layer (OL-2). A brine solution (prepared with water (85 L) and sodium chloride (34.0 Kg)) was charged to the combined organic layers (OL-1 and OL-2) at 25-30° C. The reaction mixture was stirred at 25-30° C. for 30 minutes and allowed to settle at 25-30° C. for 30 minutes. The layers were separated. The organic layer was dried over anhydrous $Na_2SO_4$. The solvent was distilled under vacuum at below 35-40° C. until 5% remained. Methanol (25.5 L) was charged to the reaction mixture at 35-40° C. and distilled until 5% remained. Methanol (61.2 L) and water (6.8 L) were charged to the reaction mixture at 35-40° C. The reaction mixture was heated to 50-55° C., stirred for 1 hour at 50-55° C., slowly cooled to 0-5° C. and maintained at 0-5° C. for 30 minutes. The solid product was filtered and washed with cold methanol (17 L).

6: To prepare the 20% Pd(OH)₂ solution, 20% Pd(OH)₂ (3.4 Kg) was added to methanol (17 L).

Product: 1,2,3,5,6,7-hexahydro-s-indacen-4-amine (16)

Off white solid
Output: 13.90 Kg (two batches)
Yield: 51.2%
1H NMR (DMSO-d6; 300 MHz): 6.33 (s, 1H), 4.50 (br s, 2H, $NH_2$), 2.70 (t, 4H), 2.57 (t, 4H), and 2.00-1.90 (m, 4H).
Moisture content (by Karl Fischer titration): 0.173%
HPLC purity: 95.43%

Purification of 1,2,3,5,6,7-hexahydro-s-indacen-4-amine (16) (Method A)

1,2,3,5,6,7-Hexahydro-s-indacen-4-amine (16) (34 Kg) was charged at 25-30° C. into a 250 L clean and dry reactor. Toluene (13.9 L) was charged at 25-30° C. and the reaction mixture was stirred at 25-30° C. for 30 minutes. Methanol (41.7 L) was charged to the reaction mixture at 25-30° C.

The reaction mixture was stirred at 25-30° C. for 30 minutes, cooled to −5 to 0° C., and stirred at −5 to 0° C. for 30 minutes. The solid product was filtered, washed with cold methanol (13.9 L), and dried at 40-45° C. for 6 hours.

Final Product:
1,2,3,5,6,7-hexahydro-s-indacen-4-amine (16)

Pale Brown Solid
Output: 11.40 Kg
Yield: 42.2%
1H NMR (DMSO-d6; 300 MHz): 6.33 (s, 1H), 4.50 (br s, 2H, NH$_2$), 2.70 (t, 4H), 2.57 (t, 4H), and 2.00-1.90 (m, 4H).
Moisture content (by Karl Fischer titration): ≤0.5%
HPLC purity: 98.43%

Reaction Scheme 2-Step i (Method B)

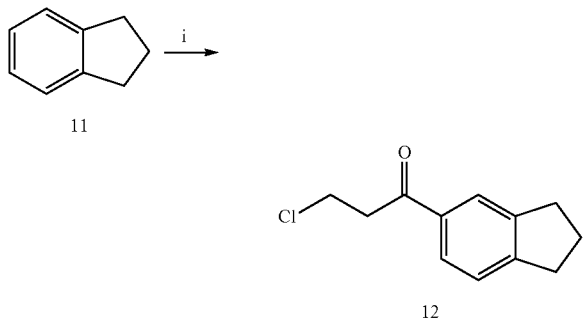

AlCl$_3$ (1.3 eq, 366.7 g) and DCM (2.5 vol, 625 mL) were charged into a round bottom flask at 25-30° C. The reaction mixture was cooled to −10 to −8° C. 3-Chloropropionyl chloride (1.1 eq, 222 mL, 140.5 g) in DCM (2.5 vol, 625 mL) was added slowly at −10 to −8° C. The reaction mixture was maintained at −10 to −8° C. for 30 minutes. Indane (11) (1 eq, 250 g) in DCM (2.5 vol, 625 mL) was added slowly drop wise at −10 to −8° C. Then the reaction mixture was heated to 25-30° C. and maintained at 25-30° C. for 12 hours. The absence of indane (11) was confirmed by HPLC (Limit: ≤2.0%).

After completion of the reaction, the reaction was quenched with 2 N hydrochloric acid solution (10 vol, 2500 mL) at 0-5° C. The reaction mixture was heated to 25-30° C. and stirred at 25-30° C. for 15 minutes. The organic layer was separated and the aqueous layer was extracted with DCM (2×5 vol, 2×1250 mL). The combined organic layers were washed with water (5 vol, 1250 mL) and dried over Na$_2$SO$_4$ (125 g). The solvent was distilled under vacuum at below 45° C. and co-distilled with n-heptane two times (2×5 vol, 2×1250 mL). n-Heptane (2 vol, 500 mL) was charged and the mixture was stirred for 1 hour. The solid product was filtered, washed with chilled n-heptane (0.5 vol, 125 mL), sucked dry, and dried at 40-45° C. under vacuum.

Final Product: 3-chloro-1-(2,3-dihydro-1H-inden-5-yl)propan-1-one (12)

Pale yellow to brown solid
Output: 360.0 g
Yield: 82%
1H NMR (DMSO-d6; 400 MHz): 7.84 (s, 1H), 7.78 (d, 1H), 7.37 (d, 1H), 3.92 (t, 2H), 3.52 (t, 2H), 2.92 (t, 4H), and 2.05 (m, 2H).
Moisture content (by Karl Fischer titration): 0.16%
HPLC purity: 98%

Reaction Scheme 2-Steps ii and iii (Method B)

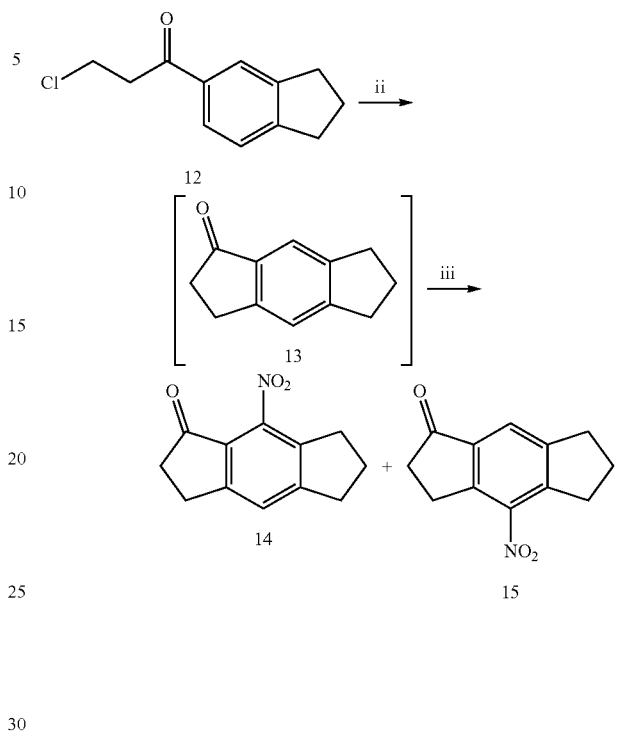

3-Chloro-1-(2,3-dihydro-1H-inden-5-yl)propan-1-one (12) (350 g) and conc. sulfuric acid (5 vol, 3185 g) were charged into a round bottom flask at 25±5° C. The reaction mixture was heated to 70±2° C. and stirred for 8-10 hours. The absence of 3-chloro-1-(2,3-dihydro-1H-inden-5-yl)propan-1-one (12) was confirmed by HPLC (Limit: ≤2.0%).

The reaction mixture was cooled to 0-5° C. A nitration mixture was prepared from conc. sulfuric acid (0.33 vol, 210.2 g) and conc. HNO$_3$ (0.5 vol, 248.5 g) at 10-15° C. The nitration mixture was added to the above reaction mixture at 0-5° C. over a period of 45-60 minutes. The reaction mixture was maintained at 0-5° C. for 2 hours. The absence of 1,2,3,5,6,7-hexahydro-s-indacen-1-one (13) was confirmed by HPLC (Limit: ≤2.0%).

After completion of the reaction, the reaction mixture was added into ice cold water (25 vol, 8.75 L) and maintained at 15±10° C. for 1 hour. The product was extracted into ethyl acetate (1×10 vol: 3.5 L, 2×5 vol: 1.75 L). The combined organic layers were washed with 10% NaHCO$_3$ solution (10 vol, 3.5 L) at 25±5° C. and dried over Na$_2$SO$_4$ (175 g). The solvent was distilled off (up to 1 vol, 350 mL) under vacuum at below 45° C. and then co-distilled with n-heptane (2 vol, 700 mL) completely. n-Heptane (2 vol, 700 mL) was added and the reaction mixture was stirred for 1 hour at 25±5° C. The solid product was filtered, washed with n-heptane (0.5 vol, 175 mL) and dried under vacuum for 2 hours at 45-50° C. The crude product was dissolved in methanol (2.0 vol, 700 mL) at 55-60° C. Charcoal 5% was added and the reaction mixture was refluxed for 1 hour and then cooled to 45° C. The reaction mixture was filtered through a hyflow bed and washed twice with methanol (2×(0.5 vol, 175 mL)). The filtrate was cooled to 0-5° C. and maintained for 2-3 hours at 0-5° C. The solid product was filtered, washed with cold methanol (0.25 vol, 87.5 mL) and dried under vacuum for 3 hours at 45-50° C.

Final Product: 8-nitro-1,2,3,5,6,7-hexahydro-s-indacen-1-one (14) and 4-nitro-1,2,3,5,6,7-hexahydro-s-indacen-1-one (15)

Brown solid
Weight ratio of 14:15 was 7:1.
Combined Output (14+15): 217 g
Combined Yield (14+15): 60%
1H NMR (DMSO-d6; 400 MHz): 7.66 (s, 1H), 3.08 (t, 2H), 2.98 (t, 2H) 2.88 (t, 2H), 2.72 (t, 2H) and 2.12 (m, 2H).
Moisture content (by Karl Fischer titration): 0.72%
HPLC purity: 96.44%

Reaction Scheme 2-Step iv (Method B)

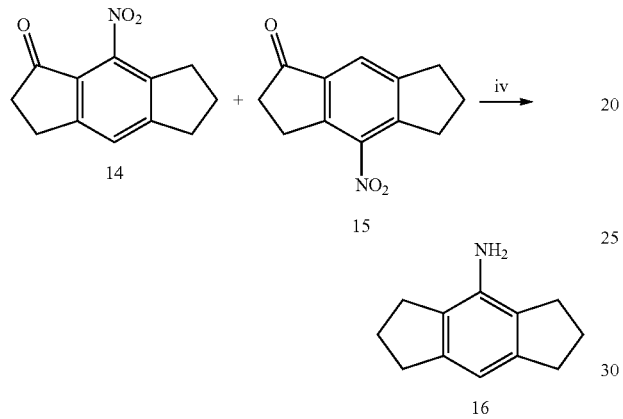

Methanol (10 vol, 250 mL) and conc. sulfuric acid (1.25 eq, 14.1 g) were charged at 25-30° C. into an autoclave. 8-Nitro-1,2,3,5,6,7-hexahydro-s-indacen-1-one (14) and 4-nitro-1,2,3,5,6,7-hexahydro-s-indacen-1-one (15) (25 g) and 10% Pd/C (5 g) (50% wet) were charged into the reaction mixture at 25-30° C. The autoclave was purged with nitrogen gas, degassed, and then hydrogen was applied at a gas pressure initially of 2-3 Kg. After 1 hour, the hydrogen gas pressure was increased to 7-8 Kg and that pressure was maintained for 12-14 hours at 25-30° C. The absence of 8-nitro-1,2,3,5,6,7-hexahydro-s-indacen-1-one (14) and 4-nitro-1,2,3,5,6,7-hexahydro-s-indacen-1-one (15) was confirmed by HPLC (Limit: ≤2.0%).

After completion of the reaction, the reaction mixture was filtered through a hyflow bed and washed twice with methanol (2×(0.5 vol, 12.5 mL)). The solvent was distilled under vacuum at below 45° C. to give an oily mass. The reaction mixture was cooled to room temperature, water (10 vol, 250 mL) was added, and the reaction mixture was stirred for 30 minutes. The product precipitated as sulfate salt which was filtered and washed thoroughly with water (5 vol, 125 mL). The wet cake and water (10 vol, 250 mL) were charged into a round bottom flask. The pH of the reaction mixture was adjusted to 10-12 with 2N NaOH solution (1.5 vol, 37.5 mL) and the reaction mixture was stirred for 30-60 minutes at 25-30° C. The precipitated solid was filtered, washed with water, sucked dry, and then dried under vacuum at 50-55° C. The crude product was dissolved in methanol-water (90:10, 5 vol, 125 mL) at 55-60° C. Charcoal (1.25 g) was added and the reaction mixture was stirred at 55-60° C. for 30-45 minutes. The reaction mixture was filtered through a hyflow bed at 45-50° C. and washed twice with methanol (2×(0.5 vol, 12.5 mL)). The filtrate was charged into another round bottom flask, cooled to 0-5° C. and maintained at to 0-5° C. for 2-3 hours. The solid product was filtered, washed with cold methanol-water (90:10, 0.5 vol, 12.5 mL), sucked dry, and dried under vacuum at 45-50° C. for 3-4 hours.

Final Product: 1,2,3,5,6,7-hexahydro-s-indacen-4-amine (16)

Pale brown solid
Output: 8 g
Yield: 45%
1H NMR (DMSO-d6; 400 MHz): 6.33 (s, 1H), 4.52 (s, 2H, NH$_2$), 2.72 (m, 4H), 2.62 (m, 4H), and 1.96 (m, 4H).
Moisture content (by Karl Fischer titration): 0.55%
HPLC purity: 99.32%

Reaction Scheme 2-Step iv (Method C)

8-Nitro-1,2,3,5,6,7-hexahydro-s-indacen-1-one (14) and 4-nitro-1,2,3,5,6,7-hexahydro-s-indacen-1-one (15) (25 g) and ethanol (10 vol, 250 mL) were charged into a round bottom flask at 25±5° C. Zn dust (10 eq, 75.25 g) was added slowly lot wise over a period of 15 minutes at 25±5° C. The reaction mixture was cooled to 15-20° C. Aqueous sulfuric acid (25%, 10 vol, 250 mL) was added slowly over a period of 30-45 minutes, while maintaining the reaction mixture temperature at 30-40° C. Then the reaction mixture was stirred at 25-30° C. for 3 hours. The absence of 8-nitro-1,2,3,5,6,7-hexahydro-s-indacen-1-one (14) and 4-nitro-1,2,3,5,6,7-hexahydro-s-indacen-1-one (15) was confirmed by HPLC (Limit: ≤2.0%).

After completion of the reaction, the reaction mixture was filtered and washed with ethanol (2×5 vol; 2×125 mL). The solvent was concentrated to 1-2 volumes (25-50 mL) under vacuum at 45-50° C. The reaction mixture was cooled to 20-30° C., water (10 vol, 250 mL) was added, and the reaction mixture was stirred for 30-60 minutes. The product precipitated as sulfate salt which was filtered and washed thoroughly with water (5 vol, 125 mL). The wet cake and water (10 vol, 250 mL) were charged into a round bottom flask. The pH of the reaction mixture was adjusted to 10-12 with aqueous 10% sodium carbonate solution (4 vol, 100 mL) and the reaction mixture was stirred for 30-60 minutes at 25-30° C. The precipitated solid was filtered, washed with water, sucked dry, and then dried under vacuum at 50-55° C. The crude product was dissolved in methanol-water (90:10, 5 vol, 125 mL) at 60-65° C. Charcoal (1.25 g) was added and the reaction mixture was maintained for 30-45 minutes at reflux. Then the reaction mixture was filtered through a hyflow bed at 45-50° C. and washed with methanol-water (90:10, 0.5 vol, 12.5 mL). The filtrate was charged into another round bottom flask, cooled to 0-5° C. and maintain at 0-5° C. for 2-3 hours. The solid product was filtered, washed with cold methanol-water (90:10, 0.5 vol, 12.5 mL), sucked dry, and dried under vacuum at 45-50° C. for 3-4 hours.

Final Product:
1,2,3,5,6,7-hexahydro-s-indacen-4-amine (16)

Pale brown solid
Output: 6.5 g
Yield: 37%
1H NMR (DMSO-d6; 400 MHz): 6.33 (s, 1H), 4.52 (s, 2H, NH$_2$), 2.72 (m, 4H), 2.62 (m, 4H), and 1.96 (m, 4H).
Moisture content (by Karl Fischer titration): 0.49%
HPLC purity: 98.29%

N-((1,2,3,5,6,7-Hexahydro-s-indacen-4-yl)carbamoyl)-1-isopropyl-1H-pyrazole-3-sulfonamide (17)

N-((1,2,3,5,6,7-Hexahydro-s-indacen-4-yl)carbamoyl)-1-isopropyl-1H-pyrazole-3-sulfonamide (17) was prepared according to the reaction illustrated in Reaction Scheme 3.

Reaction Scheme 3

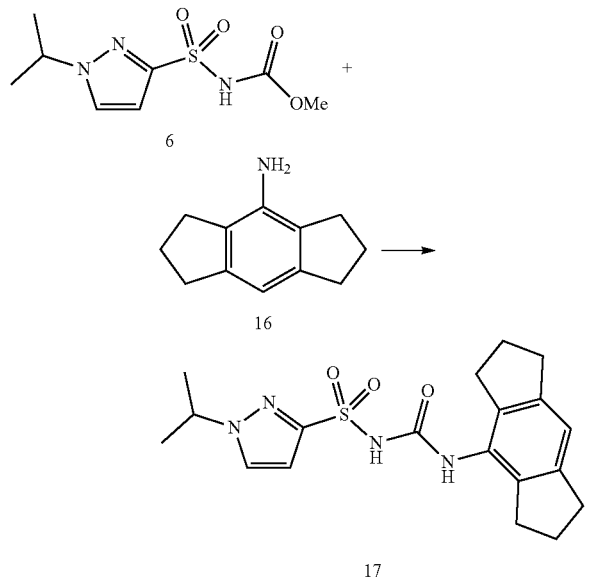

1-Isopropyl-3-(methoxycarbonylaminosulfonyl)-1H-pyrazole (6) (20.0 g, 1 eq) and 1,2,3,5,6,7-hexahydro-s-indacen-4-amine (16) (1.05 eq, 14.7 g) were suspended in dimethyl carbonate (5 vol, 100 mL) and heated to 50° C. One volume (20 mL) of solvent was distilled off in vacuo and the reaction mixture was further heated to 85° C. and stirred at 85° C. for 7 hours and 10 minutes. Another volume (20 mL) of solvent was distilled off at 85° C. and the reaction mixture was stirred at 85° C. for 19 hours. The temperature was further increased to 95° C. and stirring was continued for 5 hours before the reaction was cooled to 30° C. An IPC showed 99.3% conversion. 2-MeTHF (5 vol, 100 mL) was added slowly at 30° C. over 35 minutes. The suspension was cooled to 20° C. over 30 minutes and kept at 20° C. for another 3.5 hours. The suspension was filtered, rinsing with mother liquor, then with a mixture of 2-MeTHF/n-heptane (1:1, 4 vol, 80 mL) and with n-heptane (4 vol, 80 mL). The filter-cake was dried in vacuo to afford the product.

Final Product: N-((1,2,3,5,6,7-hexahydro-s-indacen-4-yl)carbamoyl)-1-isopropyl-1H-pyrazole-3-sulfonamide (17)

Off-white to brown solid
Output: 26.80 g
Yield: 85.3%
1H NMR (DMSO-d6; 400 MHz): 10.83 (br s, 1H), 8.06 (s, 1H), 7.99 (d, J=2.28 Hz, 1H), 6.94 (s, 1H), 6.75 (d, J=2.28 Hz, 1H), 4.62 (sept, J=6.67 Hz, 1H), 2.78 (t, J=7.22 Hz, 4H), 2.57 (t, J=7.22 Hz, 4H), 1.93 (quin, J=7.35 Hz, 4H), and 1.43 (d, J=6.84 Hz, 6H).
HPLC purity: 99.02%

N-((1,2,3,5,6,7-Hexahydro-s-indacen-4-yl)carbamoyl)-1-isopropyl-1H-pyrazole-3-sulfonamide salts N-((1,2,3,5,6,7-Hexahydro-s-indacen-4-yl)carbamoyl)-1-isopropyl-1H-pyrazole-3-sulfonamide (17) was converted into the monosodium monohydrate salt.

N-((1,2,3,5,6,7-Hexahydro-s-indacen-4-yl)carbamoyl)-1-isopropyl-1H-pyrazole-3-sulfonamide (17) (4.0 g, 1 eq) was suspended in acetone (5.5 vol, 22 mL). NaOMe in methanol (30%, 1 eq, 1.83 g) was added using a syringe (the syringe was rinsed with acetone (2 vol, 8 mL)). The turbid solution was filtered over a pad of charcoal, inline-filtered (0.45 μm) and the inline-filter was rinsed with acetone (3 vol, 16 mL). The clear brown solution was concentrated in vacuo at 45° C. to 5.1 residual volumes (20.4 mL). Water (0.4 vol, 1.62 g) was added and the suspension was heated to 45° C. MTBE (4 vol, 16 mL) was added slowly and the reaction mixture was seeded (0.5% w/w). After stirring for 30 minutes, more MTBE (6 vol, 24 mL) was added slowly over 1 hour. The suspension was stirred for a short while, before adding further MTBE (13 vol, 52 mL). The suspension was cooled to room temperature and the suspension was filtered, rinsing with mother liquor, then with a mixture of H$_2$O/acetone/MTBE (1/9/50, 2 vol, 8 mL) and with MTBE (4 vol, 16 mL). The filter-cake was dried in vacuo to afford the product.

Final Product: N-((1,2,3,5,6,7-hexahydro-s-indacen-4-yl)carbamoyl)-1-isopropyl-1H-pyrazole-3-sulfonamide monosodium monohydrate salt Off-white solid
Output: 4.01 g
Yield: 91%
1H NMR (D$_2$O; 400 MHz): 7.74 (d, J=2.53 Hz, 1H), 7.07 (s, 1H), 6.68 (d, J=2.53 Hz, 1H), 4.58 (sept, J=6.76 Hz, 1H), 2.85 (t, J=7.35 Hz, 4H), 2.67 (t, J=7.35 Hz, 4H), 2.01 (quin, J=7.35 Hz, 4H), and 1.49 (d, J=6.84 Hz, 6H).
Moisture content (by Karl Fischer titration): 5.2%
HPLC purity: 99.26%

It will be understood that the present invention has been described above by way of example only. The examples are not intended to limit the scope of the invention. Various modifications and embodiments can be made without departing from the scope and spirit of the invention, which is defined by the following claims only.

The invention claimed is:
1. A process of preparing N-((1,2,3,5,6,7-hexahydro-s-indacen-4-yl)carbamoyl)-1-isopropyl-1H-pyrazole-3-sulfonamide or a salt thereof, comprising the step of contacting

1-isopropyl-3-(alkoxycarbonylaminosulfonyl)-1H-pyrazole with 1,2,3,5,6,7-hexahydro-s-indacen-4-amine in the presence of a solvent to obtain N-((1,2,3,5,6,7-hexahydro-s-indacen-4-yl)carbamoyl)-1-isopropyl-1H-pyrazole-3-sulfonamide:

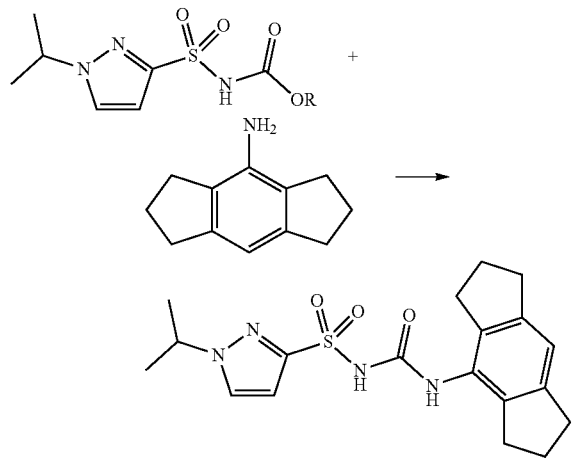

wherein R is $C_{1-6}$ alkyl.

2. The process of claim 1, wherein R is methyl.

3. The process of claim 1, wherein the solvent comprises dimethyl carbonate.

4. A process of preparing 1-isopropyl-3-(alkoxycarbonylaminosulfonyl)-1H-pyrazole:

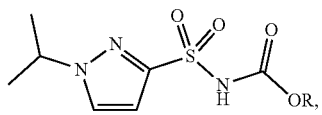

wherein R is $C_{1-6}$ alkyl, comprising one or more steps selected from:

(a) contacting 3-nitro-1H-pyrazole with iPr-X to obtain 1-isopropyl-3-nitro-1H-pyrazole, wherein X is a leaving group:

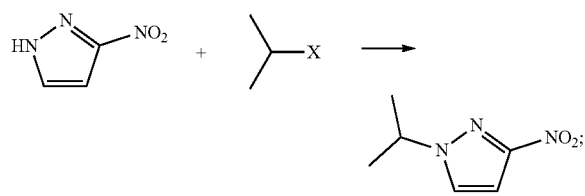

(b) reducing 1-isopropyl-3-nitro-1H-pyrazole to obtain 1-isopropyl-3-amino-1H-pyrazole:

(c) converting 1-isopropyl-3-amino-1H-pyrazole into 1-isopropyl-3-iodo-1H-pyrazole:

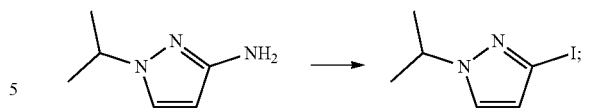

(d) converting 1-isopropyl-3-iodo-1H-pyrazole into 1-isopropyl-1H-pyrazole-3-sulfonamide:

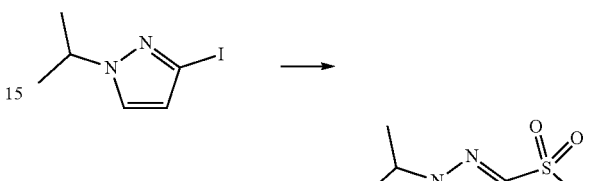

and (e) converting 1-isopropyl-1H-pyrazole-3-sulfonamide into 1-isopropyl-3-(alkoxycarbonylaminosulfonyl)-1H-pyrazole:

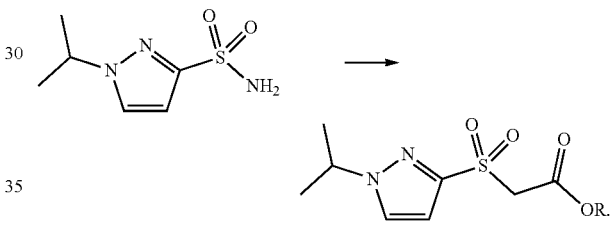

5. The process of claim 1, wherein the 1-isopropyl-3-(alkoxycarbonylaminosulfonyl)-1H-pyrazole is prepared by a process comprising one or more steps selected from:

(a) contacting 3-nitro-1H-pyrazole with iPr-X to obtain 1-isopropyl-3-nitro-1H-pyrazole, wherein X is a leaving group:

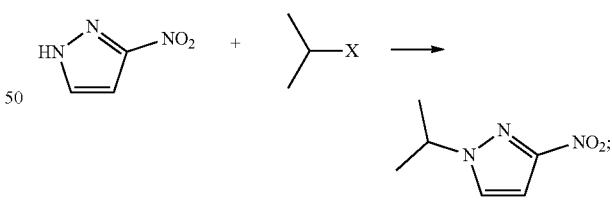

(b) reducing 1-isopropyl-3-nitro-1H-pyrazole to obtain 1-isopropyl-3-amino-1H-pyrazole:

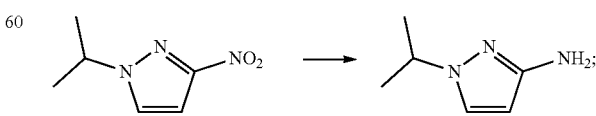

(c) converting 1-isopropyl-3-amino-1H-pyrazole into 1-isopropyl-3-iodo-1H-pyrazole:

(d) converting 1-isopropyl-3-iodo-1H-pyrazole into 1-isopropyl-1H-pyrazole-3-sulfonamide:

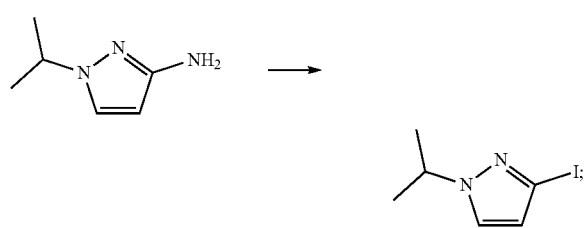

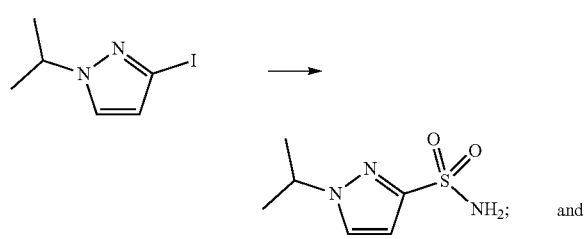 and (e) converting 1-isopropyl-1H-pyrazole-3-sulfonamide into 1-isopropyl-3-(alkoxycarbonylaminosulfonyl)-1H-pyrazole:

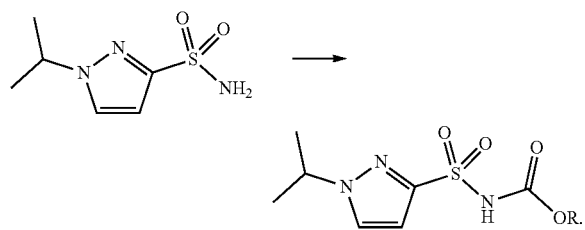

6. A process of preparing 1,2,3,5,6,7-hexahydro-s-indacen-4-amine:

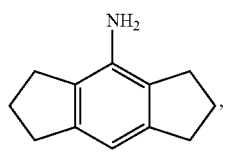 [SMILES: Nc1c2c(cc3c1CCC3)CCC2]

wherein the process is suitable for large scale clinical manufacture and comprises one or more steps selected from:

(i) contacting 2,3-dihydro-1H-indene with YCH$_2$CH$_2$COZ to obtain a substituted 1-(2,3-dihydro-1H-inden-5-yl)propan-1-one, wherein Y and Z are leaving groups:

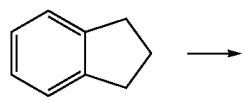

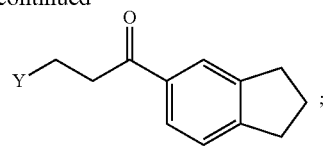

(ii) contacting the substituted 1-(2,3-dihydro-1H-inden-5-yl)propan-1-one with an acid to obtain 1,2,3,5,6,7-hexahydro-s-indacen-1-one:

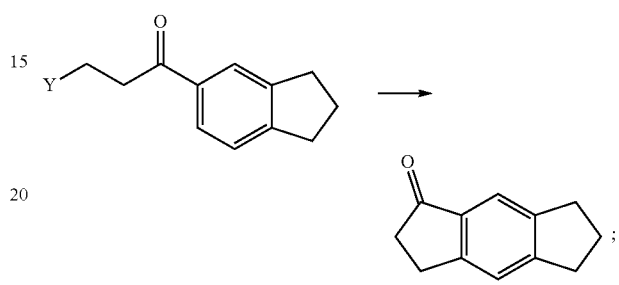

(iii) converting 1,2,3,5,6,7-hexahydro-s-indacen-1-one into 4-nitro-1,2,3,5,6,7-hexahydro-s-indacen-1-one and/or 8-nitro-1,2,3,5,6,7-hexahydro-s-indacen-1-one:

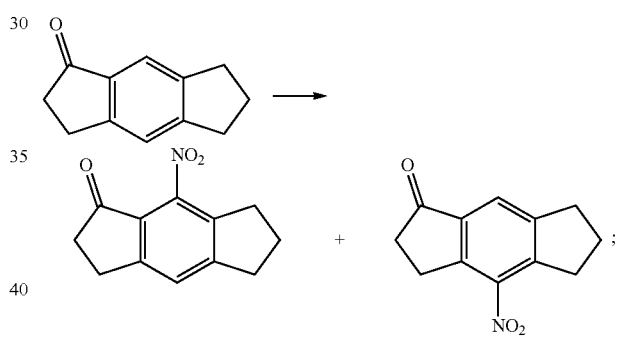

and (iv) reducing 4-nitro-1,2,3,5,6,7-hexahydro-s-indacen-1-one and/or 8-nitro-1,2,3,5,6,7-hexahydro-s-indacen-1-one to obtain 1,2,3,5,6,7-hexahydro-s-indacen-4-amine:

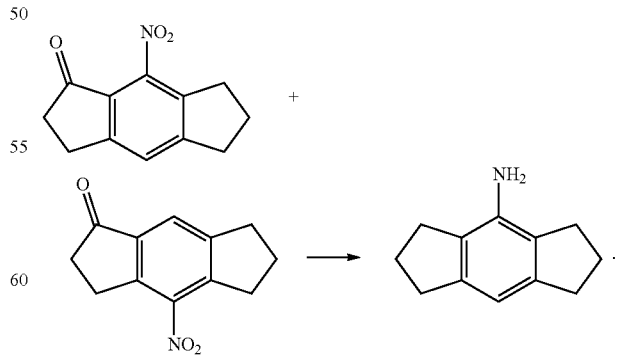

7. The process of claim 1, wherein the 1,2,3,5,6,7-hexahydro-s-indacen-4-amine is prepared by a process comprising one or more steps selected from:

(i) contacting 2,3-dihydro-1H-indene with YCH₂CH₂COZ to obtain a substituted 1-(2,3-dihydro-1H-inden-5-yl)propan-1-one, wherein Y and Z are leaving groups:

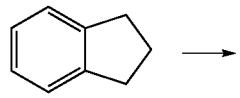

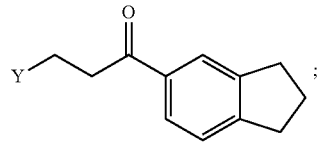

(ii) contacting the substituted 1-(2,3-dihydro-1H-inden-5-yl)propan-1-one with an acid to obtain 1,2,3,5,6,7-hexahydro-s-indacen-1-one:

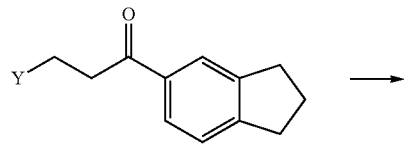

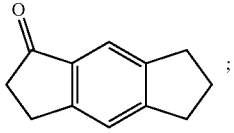

(iii) converting 1,2,3,5,6,7-hexahydro-s-indacen-1-one into 4-nitro-1,2,3,5,6,7-hexahydro-s-indacen-1-one and/or 8-nitro-1,2,3,5,6,7-hexahydro-s-indacen-1-one:

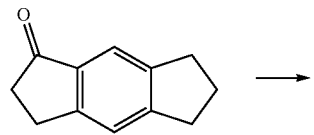

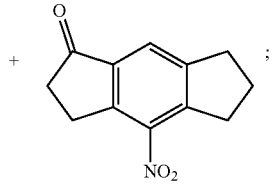

and (iv) reducing 4-nitro-1,2,3,5,6,7-hexahydro-s-indacen-1-one and/or 8-nitro-1,2,3,5,6,7-hexahydro-s-indacen-1-one to obtain 1,2,3,5,6,7-hexahydro-s-indacen-4-amine:

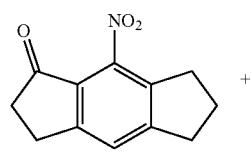

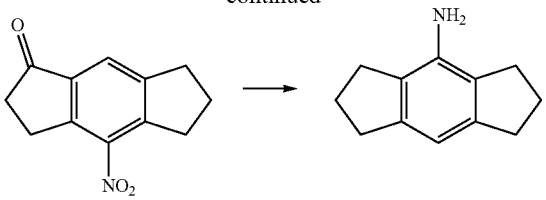

8. 1-Isopropyl-3-(alkoxycarbonylaminosulfonyl)-1H-pyrazole:

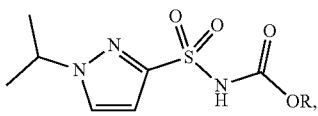

wherein R is C₁₋₆ alkyl.

9. The 1-isopropyl-3-(alkoxycarbonylaminosulfonyl)-1H-pyrazole of claim 8, wherein R is methyl.

10. The 1-isopropyl-3-(alkoxycarbonylaminosulfonyl)-1H-pyrazole of claim 8, having a HPLC purity of 98% or more, or 98.5% or more, or 99% or more, or 99.5% or more, or 99.6% or more, or 99.7% or more.

11. The process of claim 5, wherein the 1,2,3,5,6,7-hexahydro-s-indacen-4-amine is prepared by a process comprising one or more steps selected from:

(i) contacting 2,3-dihydro-1H-indene with YCH₂CH₂COZ to obtain a substituted 1-(2,3-dihydro-1H-inden-5-yl)propan-1-one, wherein Y and Z are leaving groups:

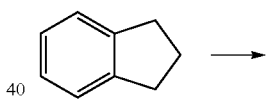

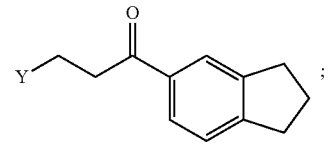

(ii) contacting the substituted 1-(2,3-dihydro-1H-inden-5-yl)propan-1-one with an acid to obtain 1,2,3,5,6,7-hexahydro-s-indacen-1-one:

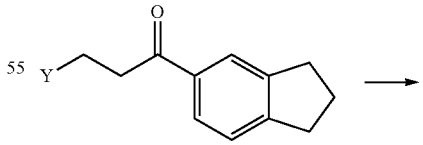

(iii) converting 1,2,3,5,6,7-hexahydro-s-indacen-1-one into 4-nitro-1,2,3,5,6,7-hexahydro-s-indacen-1-one and/or 8-nitro-1,2,3,5,6,7-hexahydro-s-indacen-1-one:

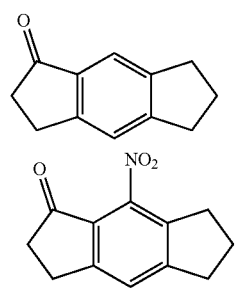 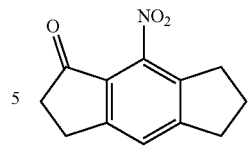
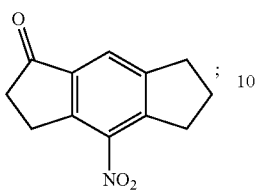
and
(iv) reducing 4-nitro-1,2,3,5,6,7-hexahydro-s-indacen-1-one and/or 8-nitro-1,2,3,5,6,7-hexahydro-s-indacen-1-one to obtain 1,2,3,5,6,7-hexahydro-s-indacen-4-amine:
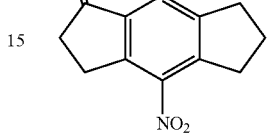 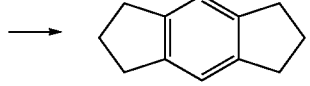
* * * * *

UNITED STATES PATENT AND TRADEMARK OFFICE
CERTIFICATE OF CORRECTION

PATENT NO. : 11,724,988 B2  
APPLICATION NO. : 17/286380  
DATED : August 15, 2023  
INVENTOR(S) : Daniel Schwizer et al.

Page 1 of 1

It is certified that error appears in the above-identified patent and that said Letters Patent is hereby corrected as shown below:

In the Claims

In Column 32, Lines 33-38, Claim 4, delete " 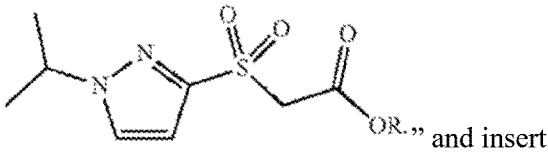 " and insert 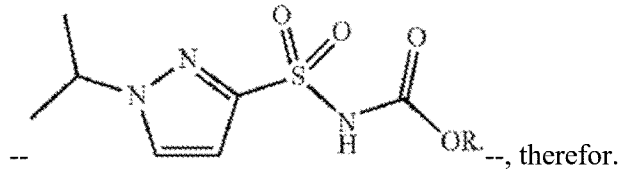 --, therefor.

Signed and Sealed this  
Twenty-seventh Day of August, 2024

Katherine Kelly Vidal  
*Director of the United States Patent and Trademark Office*